(12) United States Patent
Curtin et al.

(10) Patent No.: US 8,012,118 B2
(45) Date of Patent: Sep. 6, 2011

(54) ARTIFICIAL KIDNEY DIALYSIS SYSTEM

(75) Inventors: Conor Curtin, Westford, MA (US);
Benjamin J. Lipps, Boston, MA (US);
Norma J. Ofsthun, Lexington, MA
(US); Harold F. Sandford, Groton, MA
(US); Amanda Stennett, Waltham, MA
(US); David Updyke, Walnut Creek, CA
(US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 139 days.

(21) Appl. No.: 11/895,075

(22) Filed: Aug. 23, 2007

(65) Prior Publication Data
US 2008/0051696 A1    Feb. 28, 2008

Related U.S. Application Data

(63) Continuation-in-part of application No. PCT/US2007/005779, filed on Mar. 8, 2007.

(51) Int. Cl.
*A61M 1/00* (2006.01)
(52) U.S. Cl. .......................... 604/29; 604/5.01
(58) Field of Classification Search .............. 604/29, 604/5.01; 424/44
See application file for complete search history.

(56) References Cited

U.S. PATENT DOCUMENTS

| | | | |
|---|---|---|---|
| 3,579,441 A | 5/1971 | Brown | |
| 3,707,967 A | 1/1973 | Kitrilakis et al. | |
| 4,094,775 A | 6/1978 | Mueller | |
| 4,256,102 A | 3/1981 | Monaco | |
| 5,026,365 A | 6/1991 | Rossini et al. | |
| 5,284,470 A | 2/1994 | Beltz | |
| 5,409,903 A | 4/1995 | Polak et al. | |
| 5,549,674 A | 8/1996 | Humes et al. | |
| 5,902,336 A * | 5/1999 | Mishkin | 623/11.11 |
| 5,944,684 A * | 8/1999 | Roberts et al. | 604/5.04 |
| 6,217,859 B1 | 4/2001 | Chang et al. | |
| 6,234,991 B1 * | 5/2001 | Gorsuch | 604/29 |
| 6,706,287 B2 | 3/2004 | Ranganathan et al. | |
| 6,719,907 B2 | 4/2004 | Collins et al. | |

(Continued)

FOREIGN PATENT DOCUMENTS

DE     25 58 363     7/1977

(Continued)

OTHER PUBLICATIONS

International Search Report from International Application No. PCT/US2008/009891, mailed on Dec. 15, 2008.

(Continued)

*Primary Examiner* — Kevin C Sirmons
*Assistant Examiner* — Deanna K Hall
(74) *Attorney, Agent, or Firm* — Hamilton, Brook, Smith & Reynolds, P.C.

(57) ABSTRACT

The present disclosure relates to a wearable dialysis system and method for removing uremic waste metabolites and fluid from a patient suffering from renal disease. Uremic waste metabolites can be removed by a wearable peritoneal dialysis device that regenerates the peritoneal dialysis solution without removing positively charged, essential ions from the solution and, consequently, the patient. Fluids can be removed from the blood of the patient by an implantable fluid removing device. Fluids are delivered to the bladder and preferably removed from the body of the patient through urination. The wearable dialysis system may be operated continuously or semi-continuously and be comfortably adapted to the body of the patient while allowing the patient to perform normal activities.

32 Claims, 11 Drawing Sheets
(4 of 11 Drawing Sheet(s) Filed in Color)

U.S. PATENT DOCUMENTS

| | | |
|---|---|---|
| 6,960,179 B2 | 11/2005 | Gura |
| 7,033,498 B2 | 4/2006 | Wong |
| 7,208,092 B2 | 4/2007 | Micheli |
| 7,276,042 B2 | 10/2007 | Polaschegg et al. |
| 7,309,323 B2 | 12/2007 | Gura et al. |
| 7,332,330 B2 | 2/2008 | Humes et al. |
| 7,597,677 B2 | 10/2009 | Gura et al. |
| 2002/0052571 A1 | 5/2002 | Fazio |
| 2003/0050622 A1 | 3/2003 | Humes et al. |
| 2003/0105424 A1 | 6/2003 | Karoor et al. |
| 2003/0114787 A1 | 6/2003 | Gura |
| 2004/0019312 A1 | 1/2004 | Childers et al. |
| 2004/0082903 A1 | 4/2004 | Micheli |
| 2004/0254514 A1 | 12/2004 | Gura |
| 2005/0123529 A1 | 6/2005 | O'Loughlin et al. |
| 2006/0058731 A1 | 3/2006 | Burnett et al. |
| 2007/0060786 A1 | 3/2007 | Gura et al. |
| 2007/0179431 A1 | 8/2007 | Roberts et al. |
| 2007/0213665 A1 | 9/2007 | Curtin et al. |
| 2008/0051696 A1 | 2/2008 | Curtin et al. |

FOREIGN PATENT DOCUMENTS

| | | |
|---|---|---|
| DE | 31 10 128 A1 | 9/1982 |
| EP | 0 003 914 A2 | 9/1979 |
| EP | 0 064 393 A2 | 11/1982 |
| JP | 56051237 | 5/1981 |
| WO | WO 84/00885 | 3/1984 |
| WO | WO 95/32736 A1 | 12/1995 |
| WO | WO 97/33474 | 9/1997 |
| WO | WO 98/00172 A2 | 1/1998 |
| WO | WO 98/16171 | 4/1998 |
| WO | WO 2004/009158 A2 | 1/2004 |
| WO | WO 2004009158 A2 * | 1/2004 |
| WO | WO 2007/103411 A2 | 9/2007 |
| WO | WO 2008/024434 A1 | 2/2008 |

OTHER PUBLICATIONS

Baysal, S.H. and Uslan, A.H., "In Vitro Study of Urease/AlaDH Enzyme System Encapusulated into Human Erythrocytes and Research into its Medical Applications," *Art. Cells, Blood Subs., and Immob. Biotech.*, 30(1):71-77 (2002).

Blumenkrantz, M.J., et al., "Applications of the Redy® Sorbent System in Hemodialysis and Peritoneal Dialysis," *Artificial Organs*, 3(3):230-236 (1979).

Chang, T.M.S., "Artificial Cells with Emphasis on Cell Encapsulation of Genetically Engineered Cells," *Artificial Organs*, 22(11):958-965 (1998).

Diaz-Buxo, J.A., "Continuous-Flow Peritoneal Dialysis: Update," *Advances in Peritoneal Dialysis*, 20:18-22 (2004).

Gordon, A., et al., "Sorbent Regeneration of Peritoneal Dialysate: An Approach to Ambulatory Dialysis," *Journal of Dialysis*, 1(2):145-164 (1976-1977).

Lewin, A., "Sorbent Based Regenerative Peritoneal Dialysis System," *Dialysis & Transplantation*, 7(8):831, 833 (1978).

O'Loughlin, J.A., et al., "Degradation of Low Molecular Weight Uremic Solutes by Oral Delivery of Encapsulated Enzymes," *ASAIO Journal*, 50:253-260 (2004).

O'Loughlin, J.A., et al .,"In Vivo and in Vitro Degradation of Urea and Uric Acid by Encapsulated Genetically Modified Microorganisms," *Tissue Engineering*, 10(9/10):1446-1455 (2004).

O'Loughlin, J.A., et al, "Oral Administration of Biochemically Active Microcapsules to Treat Uremia: New Insights into an Old Approach," *J. Biomater. Sci. Polymer Edn*, 15(11):1447-1461 (2004).

Prakash, S. and Chang, T.M.S., "Artificial Cells Containing Genetically Engineered *E. Coli* DH5 Cells for Urea and Ammonia Removal in Kidney and Liver Failure," *IEEE Engineering in Medicine and Biology 17th Annual Conference*, vol. 2:1729-1730 (1995).

Roberts, M., et al., "Innovative Peritoneal Dialysis: Flow-Thru and Dialysate Regeneration," *ASAIO Journal*, 45:372-378 (1999).

Sparks, R.E., et al., "Removal of Waste Metabolites in Uremia by Microencapsulated Reactants," *Trans. Amer. Soc. Artif. Int. Organs*, XV:353-359 (1969).

Wolfe, E.A. and Chang, T.M.S., "Orally Ingested Microencapsulated Urease and an Adsorbent, Zirconium Phosphate, to Remove Urea in Kidney Failure," *The International Journal of Artificial Organs*, 10(4):269-274 (1987).

Chang, T.M.S., "A Comparison of Semipermeable Microcapsules and Standard Dialysers for Use in Separation," *Separation and Purification Methods*, 3(2): 245-262 (1974).

Chang, T.M.S., "Artificial Kidney, Artificial Liver, and Detoxifiers Based on Artificial Cells, Immobilized Proteins, and Immobilized Enzymes," in *Biomedical Applications of Immobilized Enzymes and Proteins*, T.M.S. Chang, eds. (NY: Plenum Press), pp. 281-295 (1977).

Chang, T.M.S., "Biodegradable Semipermeable Microcapsules Containing Enzymes, Hormones, Vaccines, and other Biologicals," *J. Bioengineering*, 1: 25-31 (1976).

Chang, T.M.S., "Encapsulation of Enzymes, Cell Contents, Cells, Vaccines, Antigens, Antiserum, Cofactors, Hormones and Proteins," in *Biomedical Applications of Immobilized Enzymes and Proteins*, T.M.S. Chang, eds. (NY: Plenum Press), pp. 69-90 (1977).

Chang, T.M.S., "Experimental Therapy Using Semipermeable Microcapsules Containing Enzymes and Other Biologically Active Material," in *Biomedical Applications of Immobilized Enzymes and Proteins*, T.M.S. Chang, eds. (NY: Plenum Press), pp. 147-162 (1977).

Chang, T.M.S., "Immobilization of Enzymes, Adsorbents, or Both within Semipermeable Microcapsules (Artificial Cells) for Clinical and Experimental Treatment of Metabolite-Related Disorders," *Birth Defects: Original Article Series*, IX(2): 66-76 (1973).

Chang, T.M.S., "Immobilized Enzymes and Their Biomedical Applications." in *Immobilized Enzymes, Antigens, Antibodies, and Peptides Preparation and Characterization*, H.H. Weetall, ed. (NY: Marcel Dekker, Inc.), pp. 245-292 (1975).

Colton, C.K., "Analysis of Membrane Processes for Blood Purification," *Blood Purification* 5:202-251 (1987).

Gura, V., et al., "Continuous Renal Replacement Therapy for Congestive Heart Failure: The Wearable Continuous Ultrafiltration System," *ASAIO Journal* 52(1):59-61 (2006).

Gura, V., et al., "Continuous Renal Replacement Therapy for End-Stage Renal Disease." in *Cardiovascular Disorders in Hemodialysis*, C. Ronco et al., eds. (Basel:Karger), vol. 149, pp. 325-333 (2005).

Lanza, R.P., et al., "Devices Implanted as AV Shunts." in *Pancreatic Islet Transplantation vol. III: Immunoisolation of Pancreatic Islets*, R.P. Lanza et al., eds. (R.G. Landes) 1994.

Lysaght, M.J., et al., "Filtration Rates and Pressure Driving Force in AV Filtration," *Blood Purification* 1:178-183 (1983).

Maki, T., et al., "Novel Delivery of Pancreatic Islet Cells to Treat Insulin-Dependent Diabetes Mellitus," *Clin. Pharmacokinet.* 28(6):471-482 (1995).

Shaldon, S., et al., "Continuous Ambulatory Hemofiltration," *Trans. Am. Soc. Artif. Intern. Organs* XXVI:210-212 (1980).

Notification of Transmittal of the International Search Report and the Written Opinion of the International Searching Authority, or the Declaration, from PCT/US2009/062967, mailed Jun. 25, 2010, 17 pages.

Notification Concerning Transmittal of International Preliminary Report on Patentability, from PCT/US2008/009891, mailed Mar. 4, 2010, 8 pages.

Raja, R. M., et al., "Recirculation Peritoneal Dialysis with Sorbent Redy Cartridge," *Nephron*, vol. 16, pp. 134-142 (1976).

Gordon, A., "Augmentation of Efficiency by Continuous Flow Sorbent Regeneration Peritoneal Dialysis," *Trans. Amer. Soc. Artif. Int. Organs*, vol. XXII, pp. 599-603 (1976).

Blumenkrantz, M. J., et al., "Development of a Sorbent Peritoneal Dialysate Regeneration System—A Progress Report," *Proceedings of the Fifteenth Congress of the European Dialysis and Transplant Association*, pp. 213-219 (1978).

ASN Program and Abstracts, *Journal of American Society of Nephrology*, vol. 2, (3), p. 367 (1991).

\* cited by examiner

Design of Hollow Fiber Device
Strong Acid Urea Adsorbent – No Urease

Hollow Fiber Cartridge: Ion Rejecting Skin

Design of Hollow Fiber Device
Urease + Ammonium Adsorbing Resin

FIG. 7

Summary of Wearable Peritoneal Dialysis System Component Specifications

| Molecule to be removed | Required removal quantity/day | Removed by which system component | Estimated component weight | Estimated component volume |
|---|---|---|---|---|
| Urea | 20 g/day | Urease + ion exchange resins | 230 to 400 g | 230 to 400 ml |
| Urea via GI tract | 10 g/day | Oral capsule w/urease+ ammonia binder | | |
| Phosphorus | 800 mg (26mmol/day) | Hydrous zirconium oxide | 25 g | 25 ml |
| Sulfate | 4.5 g sulfate (50 mEq/day) | Hydrous zirconium oxide | 57 g | 57 ml |
| Creatinine | 1.3 g/day | Activated carbon | 55 g | 150 ml |
| Uric acid | 400 -600 mg/day | Activated carbon | Supplied for creatinine | |
| Beta-2-microglobulin | 300 mg/day | Activated carbon | Supplied for creatinine | |
| Other organic uremic toxins | | Activated carbon | Supplied for creatinine | |
| Water | 1.5 liter/day | 1 or 2 bags PD solution | N/A | |
| Excess acid | 60- 70 mEq/day | Bicarbonate in PD solution and/or pH adjusted sorbents or anion exchange resin | N/A | |
| Calcium Magnesium | Avoid depletion | Ion selectivity | N/A | | header body flow paths transparency view cutaway view

Flow Path Model of Entire Device

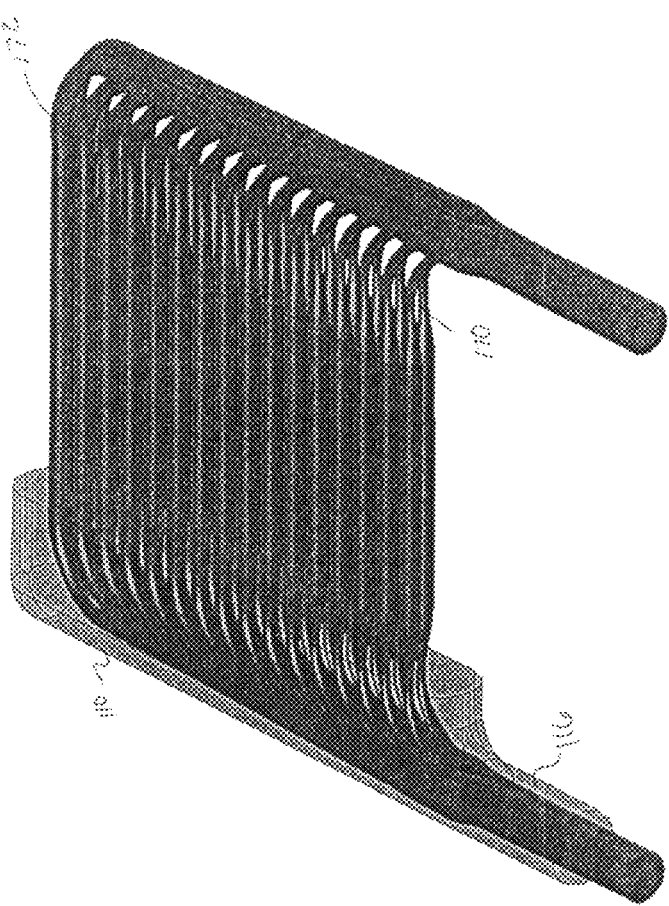

ARTIFICIAL KIDNEY DIALYSIS SYSTEM

RELATED APPLICATIONS

This application is a continuation-in-part of International Application No. PCT/US2007/005779 filed Mar. 8, 2007, which claims priority to U.S. application Ser. No. 11/371,216 filed Mar. 8, 2006. The entire contents and teachings of the above applications are herein incorporated by reference.

BACKGROUND OF THE INVENTION

Renal dysfunction or failure and, in particular, end-stage renal disease, causes the body to lose the ability to remove water and minerals and excrete harmful metabolites, maintain acid-base balance and control electrolyte and mineral concentrations within physiological ranges. Toxic uremic waste metabolites including urea, creatinine and uric acid accumulate in the body's tissues which can result in a person's death if the filtration function of the kidney is not replaced.

Dialysis is commonly used to replace kidney function by removing these waste toxins and excess water. In one type of dialysis treatment-hemodialysis-toxins are filtered from a patient's blood externally in a hemodialysis machine. Blood passes from the patient through a dialyzer separated by a semi-permeable membrane from a large volume of externally-supplied dialysate. The waste and toxins dialyze out of the blood through the semi-permeable membrane into the dialysate, which is then discarded. Hemodialysis treatment typically lasts several hours and must be performed under medical supervision three or four times a week, requirements that significantly decrease a patient's autonomy and quality of life. Also, since hemodialysis is performed periodically instead of continuously, the patient's condition and general well-being tend to be poor both immediately before (when toxin levels are high) and after (when electrolytes are imbalanced) hemodialysis, resulting in the patient having symptoms that range from nausea and vomiting to edema.

Peritoneal dialysis is another type of dialysis treatment used to replace kidney function in which sterile, pyrogen-free dialysis solution is infused into the patient's peritoneal cavity. The peritoneal membrane serves as a natural dialyzer and toxic uremic waste metabolites and various ions diffuse from the patient's bloodstream across the membrane into the dialysis solution via an osmotic gradient. The dialysis solution is removed, discarded and replaced with fresh dialysis solution on a semi-continuous or continuous basis. Although not all peritoneal dialysis systems require medical supervision in a treatment center, draining, discarding and replacing the large volumes of solution needed for peritoneal dialysis is still inconvenient, unwieldy and expensive.

To address this problem, devices have been designed that reconstitute used dialysate from hemodialysis and/or peritoneal dialysis as opposed to discarding it. The solution can be regenerated in a machine employing a device that eliminates urea from the solution. For example, the original Redy® (REcirculating DYalysis) Sorbent System (Blumenkrantz et al., *Artif. Organs* 3(3):230-236, 1978) consists of a sorbent cartridge having five layers through which dialysate solution containing uremic waste metabolites flows in order to be regenerated. The spent dialysate flows through a purification layer that removes heavy metals (i.e., copper and lead) and oxidants (i.e., chlorine and chloramine), an aluminum oxide layer containing urease bound to some of the aluminum oxide which degrades the urea in the dialysate into ammonium carbonate, a zirconium phosphate layer that adsorbs the ammonium ions produced from urea degradation along with other cations (i.e, potassium, magnesium and calcium), a hydrated zirconium oxide layer that binds phosphate and other anions (i.e., fluoride and sulfate) in exchange for acetate and an activated carbon layer that adsorbs other organic compounds (i.e., creatinine and uric acid).

Typically, the ion exchange resins used in devices such as the Redy® Sorbent System adsorb not only the urea degradation products, but also essential ions like calcium and magnesium that have diffused into the peritoneal dialysis solution. These ions must then be rapidly replaced in the patient; however, there currently exists no easy or convenient mechanism to do so. Further, although hemodialysis and peritoneal dialysis dialysate can be regenerated, no device has yet been devised that both operates continuously, clears uremic waste metabolites effectively and is small enough and/or weighs little enough to actually be comfortably worn by a patient.

Peritoneal dialysis devices may be designed to be worn by a patient suffering from renal disease. It is desirable for wearable peritoneal dialysis devices to be of light weight and small size while still providing the desired functionality and therapeutic benefits. Any reduction in the size and weight of wearable peritoneal dialysis device can make the wearable device more comfortable to wear and less cumbersome. Smaller and lighter wearable devices can substantially improve the quality of life for a patient wearing a wearable peritoneal dialysis device.

There is a need for a dialysis system that is safe and effective and that significantly improves a patient's quality of life over current systems and methods. What is required is a dialysis system that operates regularly enough such that the patient does not feel unwell for significant periods of time and one that does not consume large blocks of the patient's time, require medical supervision, require volumes of dialysate so large that the patient must practically remain stationary, nor remove essential ions and minerals from the patient that then must be replaced externally. It would also be advantageous for the system to be safe enough for a patient to use continuously and perform normal activities with little worry; that is, a system that does not involve the extracorporeal filtration of blood (e.g., hemodialysis), as a malfunction or disconnect within the blood circulation system can easily occur and result in rapid blood loss and death. In addition, it would be advantageous for any aspect of the system that is wearable to be small and light weight. Thus, there would be a great benefit to a dialysis system that truly allows a patient to function independently. Of further benefit would be a peritoneal dialysis device that is capable of reconstituting the dialysis solution without also removing essential ions from the patient.

SUMMARY OF THE INVENTION

The present disclosure provides a dialysis system that can be comfortably used by a patient continuously, 24 hours a day, 7 days a week as an alternative to conventional hemodialysis or peritoneal dialysis treatments. The dialysis system includes a wearable peritoneal dialysis device that recirculates peritoneal dialysis solution that is regenerated using a replaceable cartridge that minimizes the loss of cations from the patient. The dialysis system also includes an implantable fluid removing device that removes fluid from the body of the patient by circulating blood of the patient through the implanted fluid removal device. The dialysis treatment can be continuous or semi-continuous. The fluid removing device can be primarily directed to removing fluid from the body of the patient, reducing the load on, and the required size and weight of, the wearable peritoneal dialysis device.

Accordingly, the disclosure relates to a dialysis system that can include a wearable peritoneal dialysis device and an implantable fluid removing device. In one embodiment, the wearable peritoneal dialysis device can include a closed fluid system loop that circulates a volume of peritoneal dialysis solution for infusion into and moving out of the patient's peritoneal cavity, thereby removing from the patient uremic waste metabolites that have diffused into the peritoneal dialysis solution. The closed fluid system can circulate the peritoneal dialysis solution from the patient, throughout the wearable peritoneal dialysis device and back into the patient. Attached to the fluid system loop of the wearable peritoneal dialysis device can be: at least one pump for infusing the peritoneal dialysis solution into the patient's peritoneal cavity and moving the peritoneal dialysis solution containing uremic waste metabolites out of the patient's peritoneal cavity and into the fluid system loop; a filter for removing particulates and debris from the peritoneal dialysis solution containing uremic waste metabolites; and a urea removal device for regenerating the peritoneal dialysis solution. The filter can also remove bacterial contamination from the regenerated peritoneal dialysis solution.

In another embodiment, the urea removal device of the wearable peritoneal dialysis device of the dialysis system, can further include a replaceable cartridge. In one embodiment, the replaceable cartridge can include: a purification layer for removing heavy metals, oxidants and other uremic waste metabolites from the peritoneal dialysis solution; a urea removal layer that rejects calcium and magnesium ions; and an ion-exchange layer for removing phosphate and sulfate from the peritoneal dialysis solution. The ion exchange layer can include a polymeric phosphate binder or an inorganic sorbent.

The urea removal layer can include composition that repels cations yet allows urea to pass through. Thus, urea is removed from the patient but essential ions like calcium and magnesium are retained in the patient and other cations like sodium and potassium are prevented from accumulating in the replaceable cartridge, extending the life of the cartridge. In one embodiment, the composition that rejects cations is hollow fibers comprised of an ion-selective nanofiltration membrane, hollow fibers containing a layer of material that rejects cations, an ion-exchange membrane or an encapsulation surrounding the urea removal components, the encapsulation comprised of a material that rejects cations. The ion-rejecting material comprising the cation-rejecting composition or the encapsulant can be materials that reject cations by electrostatic repulsion, hydrophobicity, size exclusion, partitioning or a combination of the foregoing.

In addition to a composition that rejects cations, in one embodiment, the urea removal layer is also comprised of a composition that removes urea from the peritoneal dialysis solution. In one embodiment, the urea removal layer comprises a strong acid cation exchange resin that adsorbs the urea, together with a basic resin. In another embodiment, the urea removal layer is further comprised of an urea-degrading enzyme and at least one ion exchange sorbent that adsorbs the urea degradation products. In one embodiment, the urea-degrading enzyme is urease and, in another embodiment, the urease is attached to resin beads or the wall of hollow or solid fibers.

In another embodiment, the wearable peritoneal dialysis device of the dialysis system can include a microprocessor in communication with the components of the fluid system loop. The microprocessor can control the pump flow rates, the timing and sequencing of the components of the wearable peritoneal dialysis device. The microprocessor can also be designed to be controlled externally as well. The dialysis system can further include sensors for monitoring the rate of fluid removal from a patient.

In yet another embodiment, the wearable peritoneal dialysis device can include a mix container attached to the fluid system loop to re-mix the regenerated peritoneal dialysis solution with an additional osmotic agent, as needed, to achieve the required peritoneal osmotic flows.

In one aspect of the dialysis system, the wearable peritoneal dialysis device can be adapted for removal of uremic waste metabolites from the patient. In another aspect of the dialysis system, the fluid removing device can be adapted for the removal of fluid from the patient.

The present invention also relates to an integrated dialysis system that can include a wearable peritoneal dialysis device and an implantable fluid removing device. In one aspect of the integrated dialysis system, the wearable peritoneal dialysis device can be primarily adapted for removal of uremic waste metabolites from the patient. In another aspect of the dialysis system, the implantable fluid removing device can be primarily adapted for the removal of fluid from the patient. In one embodiment, the integrated dialysis system can further include sensors for monitoring the rate of fluid removal from a patient.

In another embodiment, the implantable fluid removal device of the integrated dialysis system comprises: a first header; a second header; and a filter including a plurality of hollow fiber membranes. The filter can be in fluid communication with the first header and the second header, the first header, the second header and the filter being adapted to define a flow path that provides substantially uniform flow of blood through each of the hollow fiber membranes. In one embodiment, the first header has multiple outlets and the second header has multiple inlets, and the flow path includes one or more neck regions near each of one or more of the multiple outlets and one or more of the multiple inlets.

In yet another embodiment, the first and second header are elongated members. The first header, second header and the filter can also be substantially coplanar. In another embodiment, the filter is substantially permeable to water and substantially impermeable to blood cells and proteins. The first header, the second header and the filter can also be less than approximately 10 mm in thickness.

In one embodiment, the integrated dialysis system can include a first graft for connecting the vascular system of the patient to the first header; a second graft for connecting the second header to the vascular system of the patient; a housing adapted to collect fluid that passes through the filter; and a drain conduit connected to the housing.

The invention also relates to methods for the removal of uremic waste metabolites and fluid from a patient using a wearable peritoneal dialysis device and an implantable fluid removing device. An exemplary method can include: providing a volume of peritoneal dialysis solution; pumping the peritoneal dialysis solution into the peritoneal cavity of the patient through an access port, allowing the patient's uremic waste metabolites to diffuse across the peritoneal membrane into the peritoneal dialysis solution; pumping the peritoneal dialysis solution containing uremic waste metabolites out of the patient and into the device; filtering particulates and debris from the peritoneal dialysis solution containing uremic waste metabolites; regenerating the peritoneal dialysis solution containing uremic waste metabolites; returning the regenerated peritoneal dialysis solution to the patient's peritoneal cavity; and removing fluid from the patient with a fluid removal device. The fluid removal device is preferably implanted in the patient.

In one embodiment, an exemplary method includes regenerating the peritoneal dialysis solution using a replaceable cartridge having a urea removal layer that rejects calcium and magnesium ions. In another embodiment, the exemplary method includes controlling the pump flow rates, the timing and sequencing of the components of the device using a microprocessor.

Unlike dialysis systems to date, the artificial kidney dialysis system disclosed herein provides for a dialysis system that can allow the patient to maintain a relatively normal, active lifestyle. The artificial kidney dialysis system described herein allows a wearable peritoneal dialysis device to be directed to substantially or solely remove toxins from the patient's blood. The peritoneal fluid can be continuously cleaned and reused. The need for a drain container and its emptying can be substantially reduced or eliminated. In addition, the amount of peritoneal dialysis fluid that must be incorporated into the wearable peritoneal dialysis device may be reduced. As a result of the foregoing, the wearable peritoneal dialysis device can be made smaller and lighter, and therefore be more comfortable and less cumbersome to wear. The artificial kidney dialysis system disclosed herein dramatically improves a patient's overall well-being and quality of life, freeing the patient from dialysis systems that are labor-intensive, time-consuming and/or require medical supervision for operation.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 7 is a table outlining specifications for a fluid system loop including a replaceable cartridge of the wearable peritoneal dialysis system.

FIGS. 13 and 14 are views of the flow path of an entire fluid removing device illustrating necking of the flow path.

DETAILED DESCRIPTION OF THE INVENTION

Figure 1:
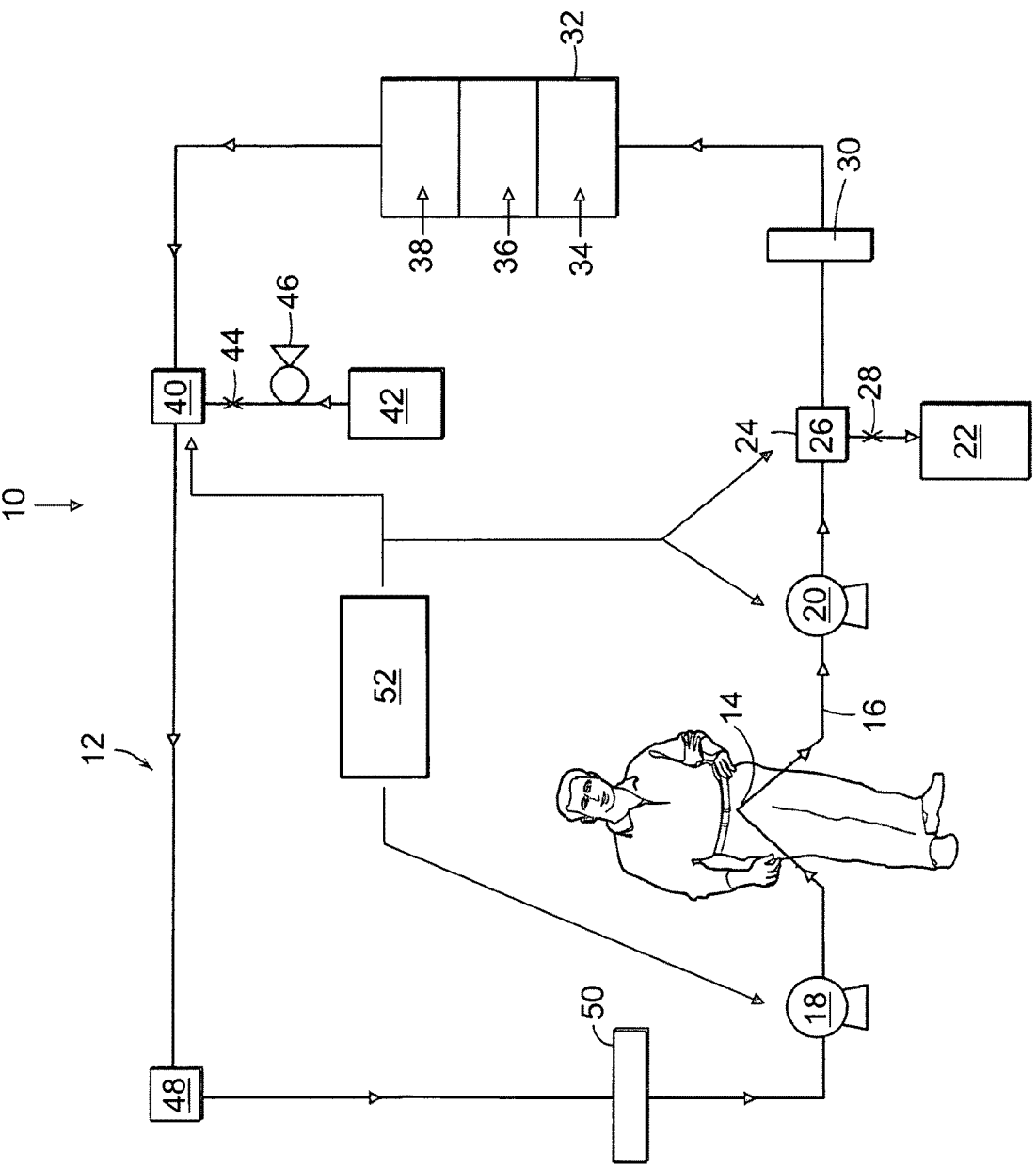
FIG. 1 is a schematic illustrating the fluid system loop of a wearable peritoneal dialysis system according to the invention.

The present invention generally relates to an artificial kidney dialysis system that includes a wearable peritoneal dialysis device or system that removes uremic waste metabolites from a patient suffering from a disorder associated with the accumulation of uremic toxins (e.g., chronic kidney failure) and an implantable fluid removing device that removes fluid from the blood of the patient and preferably delivers the fluid to the bladder so that it can be removed through natural urination. The system can be used to treat a disorder like, renal disease, for example, including early renal disease, renal dysfunction or renal failure (e.g., end stage renal disease). As used herein, the term "uremic waste metabolites" refers to compounds, such as those containing nitrogen, produced by the body as waste products and includes compounds like urea, uric acid, creatinine and β2-microglobulin and other materials (see Vanholder R. et al., *Kidney International* 63:1934-1943, 2003). Renal failure or dysfunction leads to uremic toxicity which occurs when the levels of uremic waste metabolites in a patient are elevated compared to the levels of the toxins in individuals with normal renal function.

Thus, the present invention relates to an artificial kidney dialysis system that includes a wearable peritoneal dialysis device that, unlike previous systems and devices, can be small enough in size to be wearable without significant burden to a patient 24 hours a day, 7 days a week. The peritoneal dialysis can be performed continuously or semi-continuously as the wearable peritoneal dialysis device contains a replaceable cartridge that regenerates the peritoneal dialysis solution that is then re-circulated in the wearable peritoneal dialysis device. The wearable peritoneal dialysis device is envisioned to be relatively small in size, for example, 500 to 1000 cubic centimeters (cc) in total volume. The artificial kidney dialysis system also includes an implantable fluid removing device that removes excess fluid from the blood of the patient and preferably delivers the fluid to the bladder of the patient for removal by natural urination. The fluid removing device can be primarily directed to removing fluid from the body of the patient, reducing the load on, and the required size and weight of, the wearable dialysis device. The inclusion of the fluid removing device in the artificial kidney dialysis system can enable further reductions in the size of the wearable kidney dialysis device. Alternatively, the components of the peritoneal dialysis device can also be assembled as a small or portable home use device. In this case, each component of the device may be larger or manufactured in such a way that it is useful as an in-home therapy (e.g. NxStage® or Allient® system).

Wearable Peritoneal Dialysis Device:

The wearable peritoneal dialysis device is comprised of one or more access ports coupled to a component to provide inflow to and outflow from the patient's peritoneal cavity, where the component can include medically appropriate plastic tubing, a double lumen catheter or two single lumen catheters. The wearable peritoneal dialysis system also contains a volume of peritoneal dialysis solution that is infused into and out of the patient's peritoneal cavity such that the peritoneal dialysis solution removes uremic waste metabolites that diffuse through the peritoneal membrane into the peritoneal dialysis solution. Preferably, the wearable peritoneal dialysis system continuously re-circulates the peritoneal dialysis solution for maximum mass transport of the uremic toxins across the peritoneal membrane, although periodic dwell times could be advantageous for fluid removal. Any peritoneal dialysis solution can be used (e.g., Delflex), these solutions being commercially available (e.g., Fresenius Medical Care North America) and well-known in the art. A volume of about 0.5 to 3 liters of peritoneal dialysis solution can be introduced into the wearable peritoneal dialysis system and it is preferable that about 2 liters of the solution be infused. The peritoneal dialysis solution can also comprise a material added to the solution that binds uremic toxins attached to proteins in the serum. For example, albumin can be added to the peritoneal dialysis solution in the removal of these protein-bound toxins.

Figure 2:
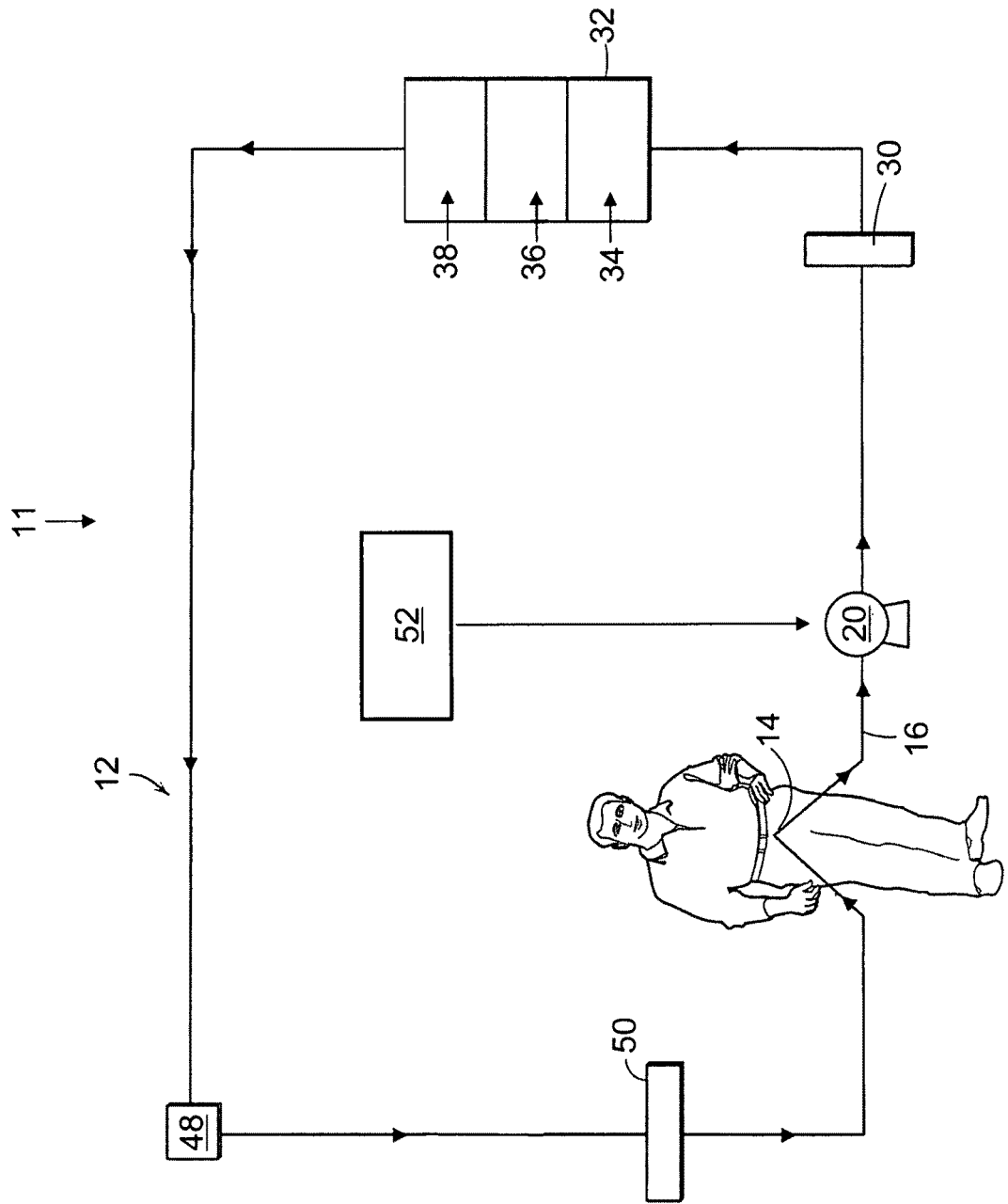
FIG. 2 is a schematic illustrating a modified fluid system loop of the wearable peritoneal dialysis system according to the invention.

Turning to FIG. 1, a wearable peritoneal dialysis system 10 is comprised of a closed, fluid system loop 12 that circulates the peritoneal dialysis solution from the patient through access port 14, throughout the components of the fluid system loop 12 along fluid path 16 and back to the patient. In one embodiment, there is at least one pump attached to the fluid system loop to both infuse peritoneal dialysis solution into the patient's peritoneal cavity and move the peritoneal dialysis solution containing uremic waste metabolites out of the peritoneal cavity and into the fluid system loop 12. There can be at least one such pump in the fluid system loop to aid in the circulation of the peritoneal dialysis solution. As shown in FIG. 1, the peritoneal dialysis solution is infused into the patient via inflow pump 18 and the peritoneal dialysis solution, containing uremic waste metabolites and other ions that have diffused into the peritoneal dialysis solution through the peritoneal membrane, is moved out of the patient via out-flow pump 20. The one or more pumps can be any small and/or miniature pumps known in the art (e.g., Harvard Shuttle Pump). In one embodiment, the peritoneal dialysis solution is pumped through the fluid loop system at a rate of about 50 to 500 milliliters/minute (mL/min). In another embodiment, the peritoneal dialysis solution is moved through the system with one pump (e.g., pump 20) (see wearable peritoneal dialysis system 11 in FIG. 2).

Also attached to fluid system loop 12 is a replaceable drain container 22 which drains excess fluid 24 that has been added to the peritoneal dialysis solution through osmosis from the patient's body. The wearable peritoneal dialysis system 10 can be further comprised of a three-way valve 26 attached to the fluid system loop 12 that is an outlet to the replaceable drain container 22 and an on-off switch 28 (between the three-way valve 26 and the replaceable drain container 22) which regulates the drainage of excess fluid 24. The drainage of the excess fluid (ultrafiltration) can occur at a rate as determined to be appropriate by the skilled artisan and preferably at a rate of about 0.5 to 2 liters per 24 hour period. The drainage of excess fluid can occur periodically with dialysis being continuous, where the patient periodically empties the excess fluid from the replaceable drain container. Alternatively, the dialysis can be performed for a specified period of time and the drainage of excess fluid can occur during a period of time subsequent to the dialysis. For example, the dialysis can be performed for 20 hours of the day and ultrafiltration for 4 hours of the day. Alternatively, dialysis can be performed 12 hours of the day with ultrafiltration occurring 4 hours of the day, leaving the peritoneal cavity free of peritoneal dialysis solution (i.e., "dry") for 8 hours of the day. Allowing the peritoneal cavity to remain dry for several hours of the day reportedly can extend the functional lifetime of the patient's peritoneal membrane. Thus, in this and other embodiments having shorter dialysis periods (e.g., 2 hours), a drain container is not required (see FIG. 2).

The wearable peritoneal dialysis system 10 can also be comprised of a filter 30 attached to the fluid system loop 12 that removes particulates, debris and, if desired, some proteins from the peritoneal dialysis solution containing uremic waste metabolites. Numerous filters of the appropriate size and molecular weight cut off (MWCO) can be used and are commercially available (e.g., Millipore). Filter 30 can be comprised of any effective membranous material, and typically would be made up of materials like cellulose, nylon, polyvinylidene fluoride, polysulfone, polyethersulfone and polypropylene. Preferably, filter 30 would be easily replaceable and/or disposable such that the filter could be changed when saturated with particulates and/or debris, for example. In one embodiment of the invention, the filter is no larger in diameter than the replaceable cartridge, such that it can be worn, and has a MWCO of about 100 kDa.

The peritoneal dialysis solution which is circulated through fluid system loop 12 continuously, is regenerated by a replaceable cartridge 32 attached to the fluid system loop. The replaceable cartridge is made up of three principal sections: a purification layer 34 that removes heavy metals, oxidants and other uremic waste metabolites from the peritoneal dialysis solution, a urea removal layer 36 that eliminates urea from the solution but rejects positively charged ions (e.g., sodium, potassium, calcium, magnesium) so that the cations are retained in the solution and an ion exchange layer 38 that removes phosphate and sulfate from the peritoneal dialysis solution (see also FIG. 3). The components of the replaceable cartridge of the invention are reduced in size compared to existing devices in order to allow the device to be easily worn on the patient's body. To be wearable, it is preferable that the dimensions of the replaceable cartridge be as small as possible to be the least obtrusive. Advantageously, the cartridge and its components can be replaced, thus when the contents of the various layers become saturated by the particular agents each layer binds and/or eliminates, the layer/section of the cartridge and/or the entire cartridge itself can be removed and easily replaced. Moreover, the sections of the device can be sterilized and/or regenerated for re-use.

Accordingly, in the replaceable cartridge, the peritoneal dialysis solution first flows through purification layer 34 which typically is comprised of activated carbon/charcoal. The solution next flows through urea removal layer 36 which is made up of urea removal components and a composition that rejects cations. As used herein, the term "urea removal components" refers to components of the replaceable cartridge that eliminate urea by adsorbing (e.g., via a strong acid cation exchange resin) or breaking down (e.g., via an urea-degrading enzyme) the urea and binding and/or removing (e.g., using a strong acid cation exchange resin or ion exchange sorbent) the byproducts of the urea elimination reactions. Urea removal layer 36 is also comprised of a composition able to reject cations that have diffused from the patient into the peritoneal dialysis solution in the patient's peritoneal cavity via a concentration gradient. The cation-rejecting composition can be comprised of ion-selective elements that prevent cations from being removed from the peritoneal dialysis solution and can include hollow fibers or membrane (e.g., a flat membrane) made of an ion-selective nanofiltration membrane, hollow fibers or a membrane coated with an ion-rejecting material, an ion-exchange membrane (e.g., Astrom® Neosepta® AFX anion exchange membrane) or an encapsulation surrounding the urea removal components.

Figure 4:
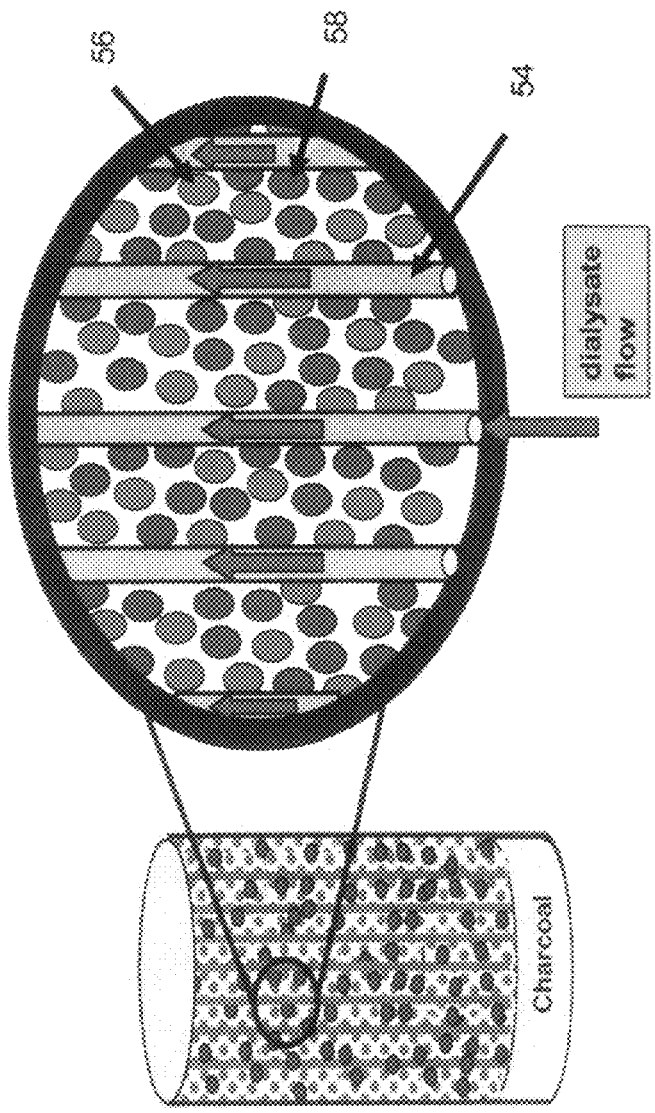
FIG. 4 is a drawing illustrating a hollow fiber device in the urea removal layer of a replaceable cartridge containing a strong acid cation exchange adsorbent and a basic resin.

Thus, in one embodiment, the urea removal layer is made up of a strong acid cation exchange resin (e.g., styrene/divinylbenzene sulfonic acid cation exchange resin) and a basic (alkaline) anion exchange resin (e.g., Dowex 1(OH)) or a dual-property resin (e.g., Bio-Rad AG 51-X8) to remove urea (see also FIG. 4). As used herein, the term "dual-property resin" refers to an ion exchange resin that can act as both a strong acid cation exchange resin and a basic (alkaline) anion exchange resin. In addition to the strong acid and basic resin(s), the urea removal layer can also be comprised of hollow fibers 54 made of an ion-selective nanofiltration membrane (available from, e.g., Amerida, Koch, GE, Hoechst and Dow) or containing a layer of a cation-rejecting material (e.g., cellulose acetate) that prevents cation diffusion from the peritoneal dialysis solution. Alternatively, in another embodiment, the ion-rejecting component can be an ion-selective encapsulation (e.g., cellulose acetate) that surrounds the strong and basic resins or the dual-property resin, the encapsulation allowing the urea through but repelling cations. In yet another embodiment, the urea removal layer can be comprised of a urea-degradation enzyme (e.g., urease) and an ion exchange resin (e.g., strong acid cation exchange) or inorganic sorbent (e.g., zirconium phosphate), the enzyme and sorbent encapsulated with a cation-rejecting material (e.g., cellulose acetate). In this embodiment also the composition that rejects cations can be comprised of hollow fibers made of an ion-selective material or hollow fibers containing a layer of an ion-rejecting material. The material covering the hollow fibers or surrounding the urea removal components would most likely be either positively charged or relatively impermeable to polar molecules, causing it to reject cations.

To complete the regeneration of the peritoneal dialysis solution, the solution then flows through ion exchange layer 38 that removes phosphate and sulfate from the peritoneal dialysis solution. The ion exchange layer can be comprised of either a polymeric phosphate binder (e.g., Renagel®) or an ion exchange sorbent (e.g., hydrous zirconium oxide). The replaceable cartridge of the wearable peritoneal dialysis system preferably removes phosphate from the patient at a rate of about 8 to 12 milliliters/minute (mL/min) and clears urea from the patient at a rate of about 10 to 30 mL/min. For the removal of 20 g of urea in 24 hours, the urea would be cleared at a rate of 10 to 15 mL/min whereas removal of 20 g of urea in 12 hours would require a urea removal rate of 20 to 30 mL/min. Sulfate is preferably cleared from the patient at a rate of about 50 milliequivalents (mEq) per 24 hours and, similarly, hydrogen ions are cleared from the patient at a rate of about 60 to 70 mEq in a 24 hour period. The regeneration of the peritoneal dialysis solution in the replaceable cartridge, which is recirculated in the wearable peritoneal dialysis system, allows a small volume of the solution to be used in the system such that it is light and compact enough to be worn by a patient with ease.

The wearable peritoneal dialysis system 10 can be further comprised of mix container 42 attached to fluid system loop 12 so that an osmotic agent (e.g., glucose, glucose polymer, amino acids) can be added, as necessary, to maintain the correct osmotic induced flow in the peritoneum. Accordingly, the wearable peritoneal dialysis system can be further comprised of a three-way valve 40 attached to the fluid system loop 12 that serves as an outlet to the mix container 42; an on-off flow switch 44 between the three-way valve 40 and the mix container 42 that regulates flow of the regenerated peritoneal dialysis solution into the container; and a flow pump 46 between the on-off switch 44 and the mix container 42 that contains a solution comprising an osmotic agent, the pump serving to infuse the osmotic agent solution into the mix container with the regenerated peritoneal dialysis solution. In one embodiment, the osmotic agent is glucose which is added to achieve or maintain a concentration of up to about 4.25 percent. In addition, the wearable peritoneal dialysis system can contain a three-way valve 48 that connects the flow of the re-mixed and regenerated peritoneal dialysis solution to an initial priming point of the fluid system loop. These components, however, are not required and, in embodiments in which the dialysis period is short and/or semi-continuous, the mix container can be eliminated (see FIG. 2).

A filter 50 able to remove bacterial contamination from the regenerated peritoneal dialysis solution can also be attached to the fluid system loop 12 of the wearable dialysis system. Filters that remove and/or eliminate bacteria are known in the art and are commercially available (e.g., JMC, A-M Systems, Millipore and Direct Med., Inc). The filter can be comprised of any material (e.g., cellulose, polyethersulfone, nylon, polyester or polystyrene) appropriate to exclude and/or sequester bacteria from the solution based on size and/or chemical or biological properties of the bacteria and would only need to be of the correct shape and size to fit appropriately in the wearable peritoneal dialysis system. Thus, the filter diameter is envisioned to be no larger than the replaceable cartridge and have a filtration cut-off of about 0.1 microns or less. Bacterial filter 50 would, preferably, also be removable, regenerable and/or replaceable.

As a means of controlling the components of the wearable peritoneal dialysis system, in one embodiment of the invention microprocessor 52 can be in communication with the components of the system (e.g., inflow pump 18, out flow pump 20, three-way valve 26 and/or three way valve 40). Microprocessor 52 can control, alter and adjust the pump flow rates and the timing and sequencing of the components of the wearable peritoneal dialysis system in response to pre-programmed instructions or according to the patient's needs as determined by the skilled clinician. The wearable peritoneal dialysis system 10 could also contain sensors able to measure uremic toxin concentrations such that microprocessor 52 can calculate relevant biostatistics (e.g., level of uremic waste metabolites removed or ions adsorbed) and be programmed to adjust accordingly the pump speed, for example, such that the patient receives the most efficacious treatment. Microprocessor 52 is preferably located within the unit housing the wearable peritoneal dialysis system 10 itself to direct and coordinate the components of the dialysis system. There could also be an external, wireless control system (e.g., another microprocessor) that could, as needed, direct and adjust the wearable peritoneal dialysis system through the microprocessor 52 that is within the wearable dialysis system unit itself.

The wearable peritoneal dialysis system can also be used in conjunction with a source of one or more enzymes capable of degrading uremic waste metabolites as described in O'Loughlin et al., *Tissue Eng.* 10:1446-1455, 2004 and O'Loughlin et al. U.S. 2005/0123529, the entire teachings of which are herein incorporated by reference. O'Loughlin et al. discloses methods to reduce the concentration of uremic toxins in vivo by either orally delivering to a patient with renal dysfunction enzymes, generally encapsulated, or organisms and/or cells capable of eliminating and/or degrading uremic toxins. A patient can orally ingest encapsulated enzymes that are able to degrade uremic waste metabolites, the metabolites degraded by the enzymes in the gastrointestinal tact. Oral administration of the enzymes in conjunction with the use of the peritoneal dialysis system decreases the load of uremic waste metabolites needing to be removed from the patient by the wearable peritoneal dialysis system, allowing the system to contain a smaller urea removal component for regenerating the dialysis solution and, consequently, be more easily worn. Further, the orally ingested enzymes, by breaking down the uremic waste metabolites, allow the smaller degradation products to be more easily removed by the wearable peritoneal dialysis system and/or the patient's intestines. The source of enzymes can include enzymes known to degrade uremic waste metabolites like uricase, urease or creatininase, or any other suitable enzymes known to one having skill in the art, or a cell naturally occurring or genetically engineered that degrades uremic waste metabolites through the expression of one or more degradation enzymes or proteins that regulate the one or more enzymes' expression or activity.

The enzymes can be administered by any suitable method including direct administration of the enzymes (e.g., as a pharmaceutical composition in an appropriate carrier), in an encapsulation (e.g., a capsule, sustained release pill or liposome) or direct administration of a cell that expresses the enzymes (e.g., a microbial, yeast or mammalian cell in a suitable carrier). In a particular embodiment, the enzymes can be encapsulated in a material like silicone, polystyrene, alginate, other polymers, cellulose, any combination of the aforementioned materials or any other medically appropriate, non-toxic material known to those of skill in the art. The encapsulation surrounding the sorbent and/or enzymes can also reject cations such that these ions are not adsorbed by the sorbent and are not removed from the patient's body. A single enzyme can be encapsulated or one or more enzymes can be encapsulated provided that the one or more enzymes are able to break down urea. The degraded uremic waste metabolites can be delivered to and eliminated by the intestines. The enzymes can be administered with a sorbent (i.e., an ion exchange sorbent like zirconium phosphate) that can adsorb the urea degradation products. In a preferred embodiment, the sorbent is encapsulated with one or more enzymes, and, in another embodiment, is in a separate encapsulation from the one or more enzymes. Generally, the sorbent would also be orally administered. If the uremic waste metabolites are degraded by a cell (e.g., a microbe), the cell itself may sequester the degradation products, which are then eliminated from the patient's body with the cell.

The amount of enzymes or cells administered to a patient to sufficiently decrease the load of uremic waste metabolites can be determined by one with skill in the art and will vary from patient to patient. The dosage will depend on the severity of the renal failure or dysfunction, the patient's age, body weight, overall well-being and the particular agent chosen under the specific conditions of administration. Preferably, the dosage does not have a negative effect on the patient. The source of the one or more enzymes can be administered once or several times during a 24 hour period, the schedule of administration dependent on the patient's need to meet a particular level of clearance of uremic waste metabolites and the patient's tolerance as determined by the skilled clinician and based on experimental models and clinical results.

Figure 3:
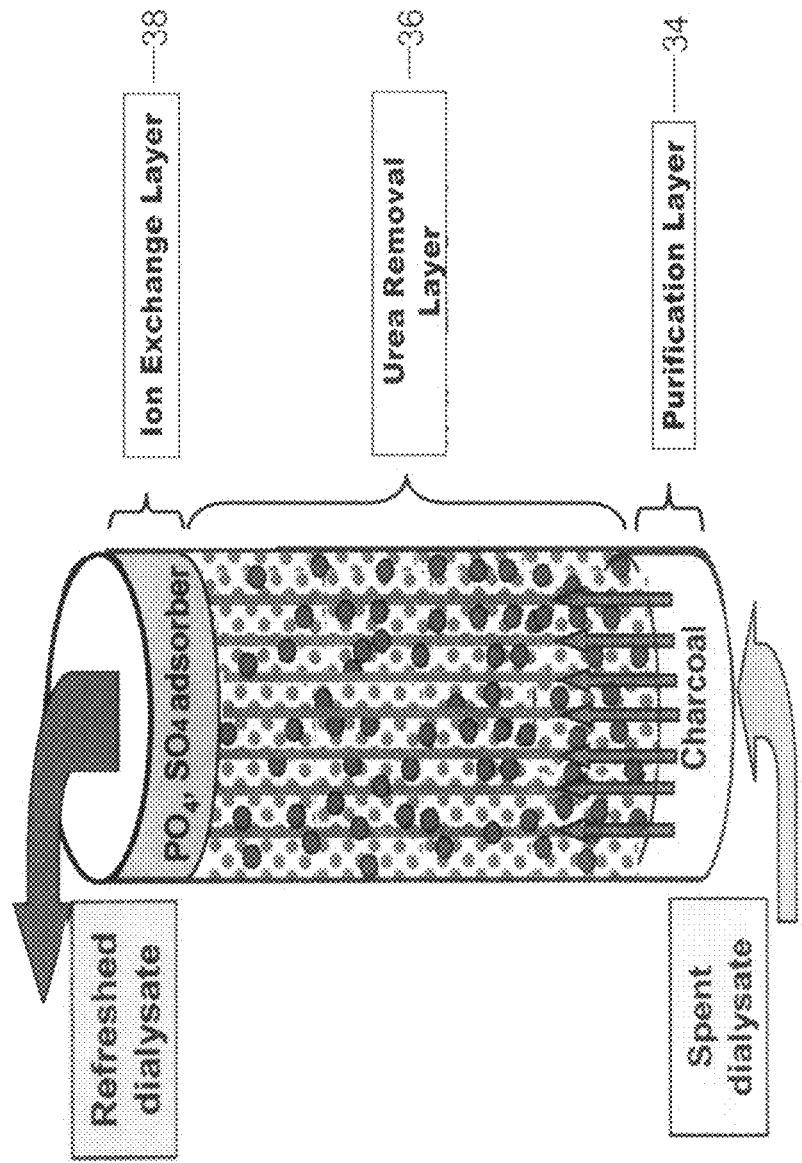
FIG. 3 is a drawing illustrating a replaceable cartridge of a wearable peritoneal dialysis system according to the invention.

The present invention further relates to a replaceable cartridge for use in the wearable peritoneal dialysis system that regenerates the peritoneal dialysis fluid in the system without adsorbing excessive amounts of cations (e.g., calcium, magnesium, sodium, potassium) that, through a concentration gradient, have diffused from the patient's body into the peritoneal dialysis solution in the peritoneum. The replaceable cartridge for use in the wearable peritoneal dialysis system contains a purification layer, urea removal layer that rejects cations in the peritoneal dialysis solution and an ion exchange layer. The cartridge and/or its components or layers can be replaced (e.g., membrane, urea-degrading enzyme), regenerated (e.g., resin, sorbent) and/or sterilized for re-use when necessary (e.g., saturation, damage, depletion). In addition, the entire cartridge can be replaceable and thus removed from the wearable peritoneal dialysis system when there is a decrease in the regeneration efficiency of the cartridge (e.g., through layer saturation) or the cartridge becomes worn or damaged, for instance. As seen in FIG. 3, peritoneal dialysis solution enters the replaceable cartridge, first encountering purification layer 34 which, like the purification layer of the device of the Redy® URS System (Renal Solutions, Inc.), removes heavy metals (e.g., lead, mercury, arsenic, cadmium, chromium and thallium), oxidants (e.g., chlorine and chloramine) and other uremic waste metabolites (e.g., creatinine and uric acid) using activated carbon, typically charcoal. Preferably, the activated carbon would have a large surface area per volume, a wide range of pore sizes for adsorbing various size uremic toxins and a high purity and/or USP grade. High purity of the carbon may be achieved through multiple acid and/or water washes to remove any water soluble impurities. It would also be advantageous for the carbon to be in a granular or pressed form in order to limit the pump power required. Examples of appropriate activated carbon include: Nuchar Aquaguard 40, Norit ROX, and Norit E Supra.

The peritoneal dialysis solution next flows through urea removal layer 36 which can, in a number of ways, eliminate urea from the solution while allowing positively charged ions and, in some cases, essential ions to be retained in it. In one embodiment, the layer is comprised of a strong acid cation exchange resin, a strong base anion resin and a composition that rejects cations. The strong acid and basic resins can be separate resins, or one dual-property mixed bead resin. Strong acid cation resins are well-known in the art (e.g., Amberlyst™ 36, 131, 15, 31, 35, 39, 40 and 70; DOWEX™ C, C-10, C-350, C-400, 650C(H), 575C NG(H), N406, G-26 (H), HCR-S/S, HCR-W2, HGR-W2, MSC, 88, M-31, MP-525C(H), DR-2030, MC-575(H), MSC-1, 88 MB and 88; Rexyn™ resins) and are commercially available (e.g., Rohm and Haas, Dow and Fisher-Scientific). Positive counter ions (e.g., hydrogen and/or sodium) may be released through the process of ion exchange in the strong acid cation resin. The released hydrogen ions are bound by a basic (alkaline) resin, to maintain the pH of the peritoneal dialysis solution in the desired (e.g., physiological) range. The basic (alkaline) resin can be any appropriate polyamine ion (e.g., anion) exchange resin available or its acid salt complex including: DOWEX 66, 77, WBA, WBA-2, WB-500, M-43, XUS 43594.00, and XUS 43568.00, Amberlite IRA67, IRA743, IRA96 and others, these resins available from Dow and Rohm and Haas, for example. As shown in FIG. 4, the strong acid and basic resins are distinct and the composition that rejects positively charged ions are hollow fibers, the hollow fibers either containing a layer of material that rejects the ions or comprised of an ion-selective nanofiltration membrane. The peritoneal dialysis solution travels through hollow fibers 54, the urea passing through hollow fibers 54 and adsorbed by strong acid cation resin 56. Basic ion exchange resin 58 helps to maintain the appropriate pH (e.g., physiological) of the solution as described above. By rejecting cations, the hollow fibers allow these ions to be retained in the peritoneal dialysis solution that is returned to the patient. Advantageously, as urea is not broken down, urea degradation products (e.g., ammonium carbonate) are not formed and thus, do not have to also be removed from the peritoneal dialysis solution.

Figure 5:
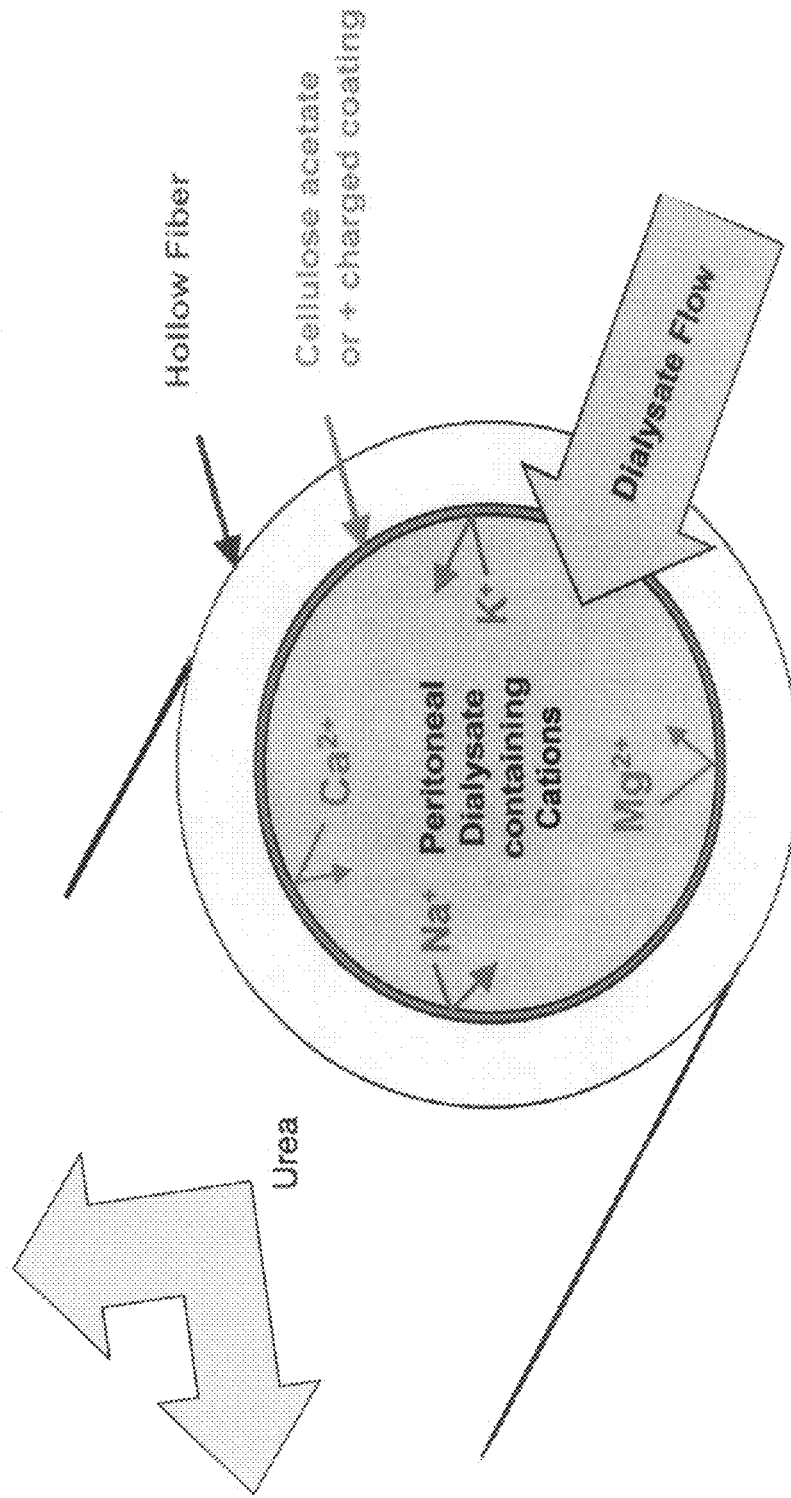
FIG. 5 is a drawing illustrating a hollow fiber in a replaceable cartridge that has a coating that repels cations.

An embodiment in which hollow fibers are fabricated from or coated with an ion-rejecting material is depicted in FIG. 5. A layer can be formed on the hollow fibers by coating or co-extruding them with a material which allows the urea through but rejects positively charged ions. The material covering the hollow fibers can be any known to one of skill in the art (e.g., fatty acids or polymer chains like cellulose acetate) that can effectively reject cations and therefore retain the ions in the peritoneal dialysis solution. Alternatively, the material can be positively charged; that is, the material can have a multitude of positively charged groups (e.g., quarternary ammonium groups) attached to a polymer film which is either coextruded with the hollow fiber material or coated on the fibers after fabrication. In one embodiment, the material used to cover the hollow fibers is cellulose acetate, in particular, cellulose diacetate and/or cellulose triacetate. Hollow fibers are commercially available (e.g., Fresenius Medical Care North America) and, for use in the invention, need only be able to be covered with the desired cation-rejecting material. Alternatively, the hollow fibers can be comprised of an ion-selective nanofiltration membrane, similar to those commercially available from a number of sources (e.g., Amerida, Koch, GE, Hoechst and Dow). These membranes have pores sizes that prevent ionic substances from diffusing through the membrane. For example, there are nanofiltration membranes that have an ability to reject ions with more than one positive charge (e.g., calcium, magnesium) while allowing single-charged ions (e.g., sodium) to pass through. In either case, the hollow fiber devices are available in a variety of dimensions and need only be small enough to fit in the replaceable cartridge, which can be sized to be comfortably worn or sized for use in an in-home system.

In another embodiment, the cation-rejecting composition can be a flat membrane that is covered with a positively charged material like those described above. In addition, the membrane can be an ion exchange (e.g., anion) membrane that limits the passage of positively charged ions (e.g., Astrom® Neosepta® AFX anion exchange membrane, PCA GmbH PC-SA anion exchange membrane). Advantageously, this ion exchange membrane also has an ability to adsorb phosphate, reducing the need for/level of phosphate-removing compositions in the ion-exchange layer of the replaceable cartridge.

In yet another embodiment, the strong acid and basic (alkaline) resins or dual-property resin (e.g., mixed bed) can themselves be encapsulated by a material through which urea can pass, but cations can not. Hence, the peritoneal dialysis solution flows into the urea removal layer comprised of the encapsulated resin(s) and the urea in the peritoneal dialysis solution diffuses through the encapsulation where it is adsorbed by the strong acid or dual-property resin. In a particular embodiment, the strong acid cation exchange resin is a sulfonic acid based resin in the protonated hydrogen (H+) form. The positive counter ions produced are adsorbed by the basic ion exchange resin also present in the encapsulation or by the dual-property resin. Cations in the peritoneal dialysis solution are prevented from passing through the ion-rejecting encapsulation. The encapsulation can be comprised of the materials previously discussed that would reject cations by electrostatic repulsion (e.g., positively charged polymers), hydrophobicity (e.g., fatty acids), size exclusion (e.g., nanofiltration), partitioning (e.g., cellulose acetate) or a combination of the foregoing properties.

Urea can also be removed from the peritoneal dialysis solution using one or more enzymes that degrade urea. Thus, in another embodiment, the urea removal layer is comprised of an enzyme that degrades urea, an ion exchange sorbent that adsorbs the urea degradation products and a composition that rejects cations, specifically, sodium, potassium, calcium and magnesium. The enzyme can be any known to one of skill in carbonate ions). Enzymes with the correct specificity and activity that can be employed are those naturally occurring (e.g., urease from jack beans, other seeds or bacteria), produced by recombinant technology (e.g., in bacterial, fungal, insect or mammalian cells that express and/or secrete urea-degrading enzymes) or produced synthetically (e.g., synthesized). In one embodiment, the enzyme is urease. In a particular embodiment, the urease is used in conjunction with a strong acid ion exchange resin (e.g., sorbent). In this embodiment, both the urease and the strong acid resin are preferably thoroughly washed of impurities/undesirable species before use in the urea removal layer of the replaceable cartridge. Both the urease and the strong acid cation exchange resin can be washed in, for example, deionized water to remove these impurities. In particular, the strong acid resin is washed to remove contaminating acidic species (e.g., free sulfonic or sulfuric acid and low molecular weight oligomeric residues of the strong acid cation exchange resin) that remain from the manufacturing process of the resin. Removal of these acidic species prevents their leaching out during regeneration of the peritoneal dialysis solution and their resultant inactivation of urease. In addition, peptide fragments or other positively charged impurities (e.g., cationic buffer species) are preferably removed from the urease by washing so that no impurities remain that may be adsorbed by the strong acid cation exchange resin, resulting in a release of hydrogen ions that decrease the pH of the environment that inactivates the urease.

The enzyme (e.g., urease) may also be chemically attached to the membrane or, alternatively, to porous beads or a resin. This both stabilizes the enzyme for extended use and, in the case of the porous beads or resin, allows the urease to be filled and/or replaced in the device. In particular, urease may be chemically attached to the exterior of the polysulfone hollow fiber membrane or to separate fibers or resins. Attachment is through reactive pendant groups of amino acid portions of the enzyme such as thiol groups, amino groups, or carboxylic acid groups that will not affect the catalytic site. Chemistries that can be used to immobilize enzymes or cross-linked enzyme crystals (CLECs) are well-known in the art (see e.g., J. Jegan Roy and T. Emilia Abraham, Strategies in *Making Cross-Linked Enzyme Crystals*, Chemical Reviews, 104(9): 3705-3721). In addition, urease can be used in its crystallized form and be mixed with the ion exchange resin or sorbent, for example, for degradation of the urea.

Figure 6:
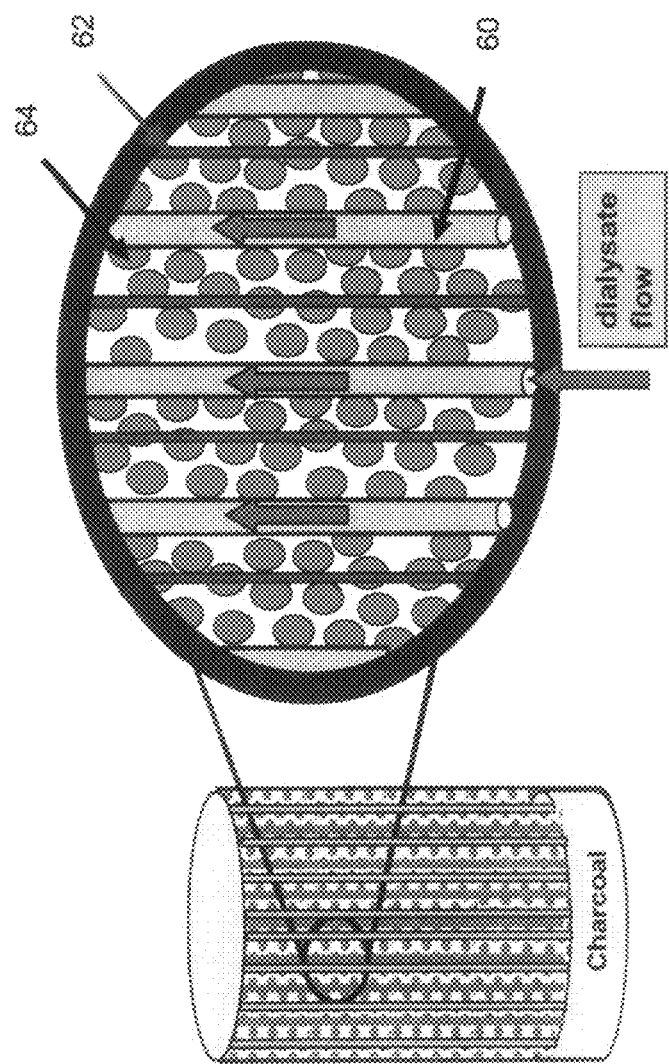
FIG. 6 is a drawing illustrating a hollow fiber device in a replaceable cartridge that contains urease to degrade urea and a sorbent to adsorb the ammonium produced by urea degradation.

In the embodiment involving the use of urea-degradation enzymes, the composition that rejects cations can similarly be a flat membrane or hollow fibers containing an ion-rejecting material or a flat membrane, hollow fibers comprised of an ion-selective nanofiltration membrane or an ion exchange membrane as described above. Alternatively, the cations can be rejected by an encapsulation surrounding the urea degrading enzyme and an ion exchange sorbent or resin. In the embodiment shown in FIG. 6, peritoneal dialysis solution containing urea flows through hollow fibers 60. Urea passes through hollow fibers 60, where encapsulated enzymes 62 break down the urea into ammonium and carbonate, the urea degradation byproducts absorbed by ion exchange sorbent 64. The sorbent (e.g., a cation exchange resin) adsorbs the ammonium ions or free ammonia. In a preferred embodiment, the ion exchange sorbent is a strong acid cation exchange resin in the protonic form, but can be any ion exchange sorbent (e.g., zirconium phosphate) that can effectively adsorb urea degradation products. As in the previous embodiment with the strong acid and basic (alkaline) resins, hollow fibers 60 allow the urea in the peritoneal dialysis solution to diffuse through and reject positively charged ion's in the solution. If the urea-degrading enzyme and ion exchange sorbent(s) are surrounded by an ion-selective encapsulation (as opposed to the urea removal layer containing hollow fibers), the urea in the peritoneal dialysis solution diffuses through the encapsulation, where it is degraded by the enzyme, and those degradation products are then bound by the ion-exchange sorbent. The ion-selective encapsulation rejects the cations in the peritoneal dialysis solution, so that they are retained in the solution. The ion-rejecting material coating the hollow fibers or comprising the encapsulation surrounding the enzyme and ion exchange resin would typically do so by electrostatic repulsion, hydrophobicity, size exclusion, partitioning or a combination of the aforementioned factors.

The replaceable cartridge is further comprised of ion exchange layer 38 (see FIGS. 1 and 2), which is designed to remove phosphate and sulfate from the peritoneal dialysis fluid after urea removal. The ion exchange layer can be comprised of those ion exchange resins able to remove phosphate and/or sulfate, for example, a strong base anion exchange resin and other applicable forms of the resin such as carbonate, bicarbonate or chloride. These resins are known to the skilled artisan who can determine the most favorable resin for use in the invention based on a number of factors, including the patient's condition and the physiological advantages of using a particular resin and the potential toxicity of the resin. For instance, the ion exchange resin can be a polymeric/polyamine phosphate binder like sevelamer hydrochloride (i.e., Renagel®, Genzyme, Inc.), poly(allylamine) and/or poly(allylamine hydrochloride). Other commercially available ion exchange resins useful for binding phosphate include: DOWEX M-43 (anion exchange resin), DOWEX 21 K XLT, DOWEX 1 (OH), DOWEX Marathon MSA and DOWEX M4195 (in the copper form). Alternatively, the ion exchange layer can be comprised of an anion exchange resin that would bind phosphate and sulfate (e.g., Amberlite™ 96, Rohm and Haas) and, in a particular embodiment, is hydrous zirconium oxide (e.g., zirconium oxide in the acetate counter ion form combined with zirconium carbonate).

Thus, after flowing through the replaceable cartridge of the invention, the peritoneal dialysis solution is essentially regenerated for reuse. The solution is largely free of urea, uric acid and creatinine, and has lower levels of phosphate and sulfate. Due to the design of the urea removal layer such that its components reject particular ions, the peritoneal dialysis solution retains sufficient levels of calcium and magnesium ions in the patient, eliminating the need for a mechanism to replace these ions in the patient. In addition, repelling cations like sodium and potassium prevents the ions from entering the replaceable cartridge, decreasing the load of ions bound to the cartridge components (e.g., the strong acid cation exchange resin of the urea removal layer) and the frequency at which the components need to be replaced/regenerated. Thus, the rejection of sodium and potassium increases the longevity of components of the replaceable cartridge and/or that of the replaceable cartridge itself.

FIG. 7 presents an example of uremic toxins and the amount of various materials calculated to be necessary to remove the uremic toxins. In general, the metabolism of most dialysis patients produces 20 g of urea on a daily basis. In an embodiment in which a patient is treated with dialysis over a 12 hour period of time, hydrolysis of 20 g of urea requires at least 1000 international units (IU) of urease (1 mg). This calculation regarding the amount of urease to be used for a particular time period of dialysis is dependent on several factors including, for example, the patient's metabolism and urea levels, the purity of the urease and the activity of the urease throughout the course of the treatment and the determination of the level of urease to use in treatment of a given patient best done by the skilled artisan. The hydrolysis of 20 g of urea by the urease generates approximately 11.4 g of ammonia. It is necessary to remove this ammonia with, for example, an ion exchange resin, in this case with 230 g of a high capacity strong acid cation exchange resin or with 1200 g of zirconium phosphate. More of the strong acid cation exchange resin can be used in the instance that the resin is exposed to other cations. To maintain a neutral pH of the solution, the acid produced from the strong acid cation exchange resin and the patient themselves must be neutralized. Generally, an alkaline anion exchange resin is utilized to neutralize the acid and, as shown in FIG. 7, 70 g of the resin is used. Inclusion of sodium bicarbonate at levels best determined by one of skill in the art can help reduce the amount of anion exchange resin required to neutralize the acid/achieve neutral pH.

Excess phosphorous (phosphate) and sulfate are released from protein catabolism and food digestion. In people with normal kidney function, any excess phosphorous and sulfate are excreted by the kidneys; however, patients with kidney disease/renal insufficiency may have up to 800 mg of excess phosphorous and/or 4.5 g of excess sulfate. In the specifications shown in FIG. 7, approximately 25 g of hydrous zirconium is used to bind the estimated 800 mg phosphorous (2.4 g phosphate) and 57 g of additional hydrous zirconium oxide used to bind the 4.5 g of sulfate.

A significant number of other uremic toxins, for example, creatinine can also be removed in dialysis. In this embodiment, 55 g of high activity (activated) high surface area carbon is used to bind 1.3 g of creatinine. This activated carbon can also remove uric acid (400 to 600 mg), $\beta$-2 microglobulin (up to 300 mg) and other uremic toxins.

In the replaceable cartridge, one of skill in the art can choose the appropriate component/materials described previously to be utilized in the urea removal layer that allows for the diffusion of urea, but excludes the passage of cationic species (e.g., calcium, magnesium) across the membrane. This design of the replaceable cartridge protects the cation exchange resin from exposure to cations which reduces the release of hydrogen ions helping to prevent changes in pH. Thus, only the amount of cation exchange resin necessary to bind the ammonia present is required. The component/material also eliminates and/or reduces the loss of these cations from the patient and the resultant need to replace them fairly quickly.

The invention further relates to methods for the removal of uremic waste metabolites from a patient using a wearable peritoneal dialysis system. The method comprises providing a volume of peritoneal dialysis solution to the patient; pumping the peritoneal dialysis solution into the peritoneal cavity of the patient through one or more access ports and allowing the patient's uremic waste metabolites to diffuse across the peritoneal membrane into the peritoneal dialysis solution; draining excess fluid into a replaceable drain container; filtering particulates and debris from the peritoneal dialysis solution containing uremic waste metabolites; regenerating the peritoneal dialysis solution containing uremic waste metabolites using a replaceable cartridge, the cartridge having an urea removal layer that rejects cations; and returning the regenerated peritoneal dialysis solution to the patient's peritoneal cavity.

The access port(s) through which the peritoneal dialysis solution is added and removed can be at a convenient and appropriate place in the patient's peritoneal cavity and can be connected to the wearable peritoneal dialysis system by any appropriate medical tubing, a double lumen catheter or a single lumen catheter. The volume of peritoneal dialysis solution initially provided in the wearable peritoneal dialysis system can be anywhere from 0.5 to 3 liters, or whatever volume deemed to be suitable to effectively clear uremic waste metabolites from the patient by one with skill in the art. The peritoneal dialysis solution is pumped through the wearable peritoneal dialysis system at a rate of about 50 to 500 mL/min and the dialysis can occur continuously or semi-continuously. In a particular embodiment of the method, drainage of excess fluid from the patient occurs at a rate of about 0.5 to 3 liters per 24 hour period. If the wearable peritoneal dialysis system operates continuously, as in one embodiment of the invention, the drainage of excess fluid can also be continuous, with excess fluid being periodically removed from the replaceable drain container by the patient. Alternatively, the wearable peritoneal dialysis system can operate semi-continuously for a specific period of time (e.g., 12 to 20 hours) and the removal of excess fluid takes place during a period of time subsequent to the dialysis (e.g., 4 hours). Preferably, some fresh dialysis fluid is added to the wearable peritoneal dialysis system once a day at a convenient time.

The peritoneal dialysis solution provided is regenerated by a replaceable cartridge having a urea removal layer that rejects cations. As before, regeneration of the peritoneal dialysis solution can decrease the amount of solution necessary to perform the dialysis and, accordingly, the size of the wearable peritoneal dialysis system. The replaceable cartridge is as described previously and regenerates the peritoneal dialysis solution through the use of a series of layers in the device, one which removes heavy metals, oxidants and other uremic waste metabolites from the solution in a purification layer, another eliminating urea from the solution without removing essential ions in a urea removal layer and yet another removing phosphate and sulfate from the peritoneal dialysis solution in an ion exchange layer. The components of the replaceable cartridge that perform these functions are also those described previously, that is, activated carbon (in the purification layer), a polymeric phosphate binder or an ion exchange sorbent (in the ion exchange layer) and urea removal components (e.g., strong acid cation exchange resin and basic (alkaline) resin(s) or urea-degrading enzymes and an ion exchange sorbent) together with a composition that rejects cations (e.g., flat membrane/hollow fibers containing a layer of a cation-rejecting composition, flat membrane/hollow fibers comprised of an ion-selective nanofiltration membrane, an ion-exchange membrane or an encapsulation surrounding the urea removal components) (in the urea removal layer). In a preferred embodiment, the cation-rejecting layer of the flat membrane or hollow fibers or surrounding the resins and/or enzymes is positively charged, containing a substituent such as quarternary ammonium group, or the material is cellulose diacetate or cellulose triacetate, fatty acids or other appropriate polymers.

In addition, the method can further comprise orally administering to a patient a source of one or more enzymes capable of degrading uremic waste metabolites, enzymes like uricase, urease or creatininase. In doing so, the load of uremic waste metabolites that need to be removed from the patient by the wearable peritoneal dialysis system can be significantly reduced in amount or altered for ease of removal and/or intestinal elimination. The source of the orally administered enzymes can be the one or more enzymes themselves in an acceptable pharmaceutical carrier and/or in a suitable encapsulation, or naturally occurring or genetically engineered cells that can degrade uremic waste metabolites as described previously. Preferably, the enzymes together with the sorbent are administered in an encapsulated form and in some cases, this encapsulation can also reject calcium and magnesium ions. The amount and/or dosage of the source of uremic toxin-degrading enzymes administered to the patient can be appropriately determined by one with skill in the art, and is dependent on the formulation chosen, the assessed necessity to clear a particular amount of uremic waste metabolites from the patient and the patient's specifications (e.g., age, body weight and overall well-being).

The method preferably results in urea being cleared from the patient at a rate of about 10 to 30 mL/min and phosphate being cleared from the patient at a rate of about 8 to 12 mL/min. Sulfate is preferably cleared from the patient at a rate of about 50 mEq per 24 hours and hydrogen ions are preferably cleared from the patient at a rate of about 60 to 70 mEq in a 24 hour period.

In yet another embodiment of the method, an appropriate osmotic agent is added to the regenerated peritoneal dialysis solution in a mix container to ensure proper osmotic induced flow into the patient's peritoneal cavity. Accordingly, the method further comprises infusing a concentrated osmotic agent solution into the mix container via a flow pump between the on-off switch and the mix container, the pump regulating the flow of the regenerated peritoneal dialysis solution into the mix container; mixing the regenerated peritoneal dialysis solution with the osmotic agent solution in the mix container; and pumping the re-mixed and regenerated peritoneal dialysis solution back into the wearable peritoneal dialysis system.

In a further embodiment of the method, the re-mixed and regenerated peritoneal dialysis solution is filtered to remove bacterial contamination from the solution. In yet another embodiment, the re-mixed and regenerated peritoneal dialysis solution flows through a three-way valve into an initial priming point of the wearable peritoneal dialysis system before the peritoneal dialysis solution is returned to the patient's peritoneal cavity.

To consistently and efficiently remove uremic waste metabolites from a patient, control of the wearable peritoneal dialysis system and, in particular, the pump flow rates and the timing and sequencing of the components of the dialysis system are electrically controlled. In a preferred embodiment, the control mechanism is a microprocessor which is part of a unit containing the wearable peritoneal dialysis system that is under its own control; however, the microprocessor can also be controlled wirelessly, typically by another microprocessor.

Artificial Kidney Dialysis System with Wearable Kidney and Implantable Fluid Removing Device Certain embodiments of the wearable peritoneal dialysis device disclosed herein may result in fluids from the patient being transferred from the patient's body to the peritoneal dialysis solution through osmosis. These "excess fluids" may be removed from the body with the peritoneal dialysis fluids. Further, these excess fluids may be removed from the wearable peritoneal dialysis device by use of the replaceable drain container. However, it can be desirable to remove additional fluid from the body so that, for example, the patient can increase his or her fluid intake.

Hemoconcentrators and other similar devices may be used to remove fluids from blood. One embodiment of such a fluid removing device is described in International Application No. PCT/US2007/018636 and WO2008/024434, entitled "Device For Removing Fluid From Blood In A Patient", filed on Aug. 23, 2007, which is incorporated herein by reference as if fully set out herein. In particular, WO2008/024434 describes embodiments of fluid removing devices that can be used to remove fluids (including water) from the body of the patient. While some uremic waste metabolites can be removed through use of the a wearable kidney device of the invention, these devices (e.g., hemoconcentrators) are primarily directed to the removal of fluid from the body.

Fluid removing devices can be adapted to be implanted into the body of the patient. Particular embodiments of such fluid removing devices are described in WO2008/024434 (see e.g., FIGS. 1, 5, 8, 15 and 16 therein). Fluid is removed from the blood stream and is delivered to the bladder by the fluid removing device, whereby it can be removed from the patient through normal urination.

An artificial kidney dialysis system can include a wearable peritoneal dialysis device as disclosed herein and a preferably implantable device that is primarily directed to remove fluid from the body of the patient. The wearable peritoneal dialysis device can be used to remove uremic waste metabolites from the body of a patient that suffers from a condition such as chronic kidney disease or kidney failure. Preferably, the fluid removing device is implantable and can be used to remove excess fluids from the body of a patient. In combination, both uremic waste metabolites and fluid can be removed from the body of a patient at rates and amounts desirable in consideration of the patient condition, as determined by one of skill in the art.

There are substantial benefits to the artificial kidney dialysis system described herein. Peritoneal dialysis is efficient at removing uremic waste metabolites, but it is generally not as efficient as hemodialysis at removing fluid from a patient. Standard hemodialysis is efficient at removing both fluids and uremic waste metabolites from blood, but it typically involves removing blood from the patient's body, requiring the patient receive treatment in a fixed location, and administration of significant amounts of anticoagulants. The artificial kidney dialysis system described herein (i) utilizes an advantageous feature of peritoneal dialysis, that is, the ability to remove uremic waste metabolites, without the requirement that it efficiently remove fluids from a patient and (ii) utilizes one of the advantageous features of hemodialysis, the efficient removal of fluid from a patient. Thus, the artificial kidney dialysis system removes uremic waste metabolites and additional (e.g., excess) fluid without many of the associated risks and limitations of peritoneal dialysis and hemodialysis.

The artificial kidney dialysis system described herein allows the wearable peritoneal dialysis device to be directed to substantially or solely remove toxins from the patient's blood. The peritoneal fluid can be continuously cleaned and reused. The need for a drain container and its emptying can be substantially reduced or eliminated. In addition, the amount of peritoneal dialysis fluid that is incorporated into the wearable peritoneal dialysis device can be reduced. As a result of the foregoing, the wearable peritoneal dialysis device can be made smaller and lighter. The patient can have a substantially increased quality of life, with less concerns and time spent attending to emptying a drain container, and a less cumbersome wearable peritoneal dialysis device. The patient can remove fluid through the natural act of urination. The artificial kidney dialysis system described herein can provide the desired therapeutic benefits and an improved patient quality of life.

In the artificial kidney dialysis system, operation of a fluid removing device can be adjusted to optimize patient health including patient fluid volumes in coordination with the operation of the wearable peritoneal dialysis device. For example, the amount of fluid removed and the rate of removal by a fluid removing device can be adjusted based on the amount of excess fluid removed (if any) by operation of a wearable peritoneal dialysis device. Such adjustment can be made by turning the device on or off. Alternatively, the wearable peritoneal dialysis device operation can be adjusted to optimize patient health including patient fluid volumes and the rate of removal in coordination with the operation of a fluid removing device. For example, more osmotic agent can be used in order to increase the rate of removal of excess fluids. As another example, the wearable kidney can be turned on or off to adjust the removal of excess fluids. In yet another example, the rate at which the peritoneal dialysis solution is pumped through the fluid loop system can be increased or decreased in order to adjust the rate of removal of excess fluids. The foregoing and other such adjustments can be made as described herein (see also WO2008/024434).

Sensors can be used to measure the amount of fluid removed and the rate of removal in connection with the operation of a fluid removing device and/or a wearable peritoneal dialysis device. The data from the sensors can be used to adjust the operation of one or both of a fluid removing device and the wearable peritoneal dialysis device. The adjustments can be made by the patient and/or a healthcare professional. Alternatively the devices can be modified automatically. Automatic modification can be made by use of one or more control systems, preferably miniature (e.g., a microprocessor), that can be located proximate to a fluid removing device and/or a wearable peritoneal dialysis device. Preferably a microprocessor and standard d/A hardware is programmed for automatic control of fluid removal to ensure proper patient hydration. Alternatively, such control systems (excluding any sensors and actuators) can be located externally, such as on a desktop computer. In such an event, sensor data can be transferred to the control system wirelessly or through use of a USB device.

A fluid removing device can be implemented for the patient at the same time as a wearable peritoneal dialysis device is implemented for such patient. Alternatively, the devices can be implemented at different times. Depending on the embodiments, they can be part of an integrated device, or can constitute separate devices. The artificial kidney dialysis system can provide an integrated solution and therapy to renal patients, substantially improving patient quality of life.

Figure 8:
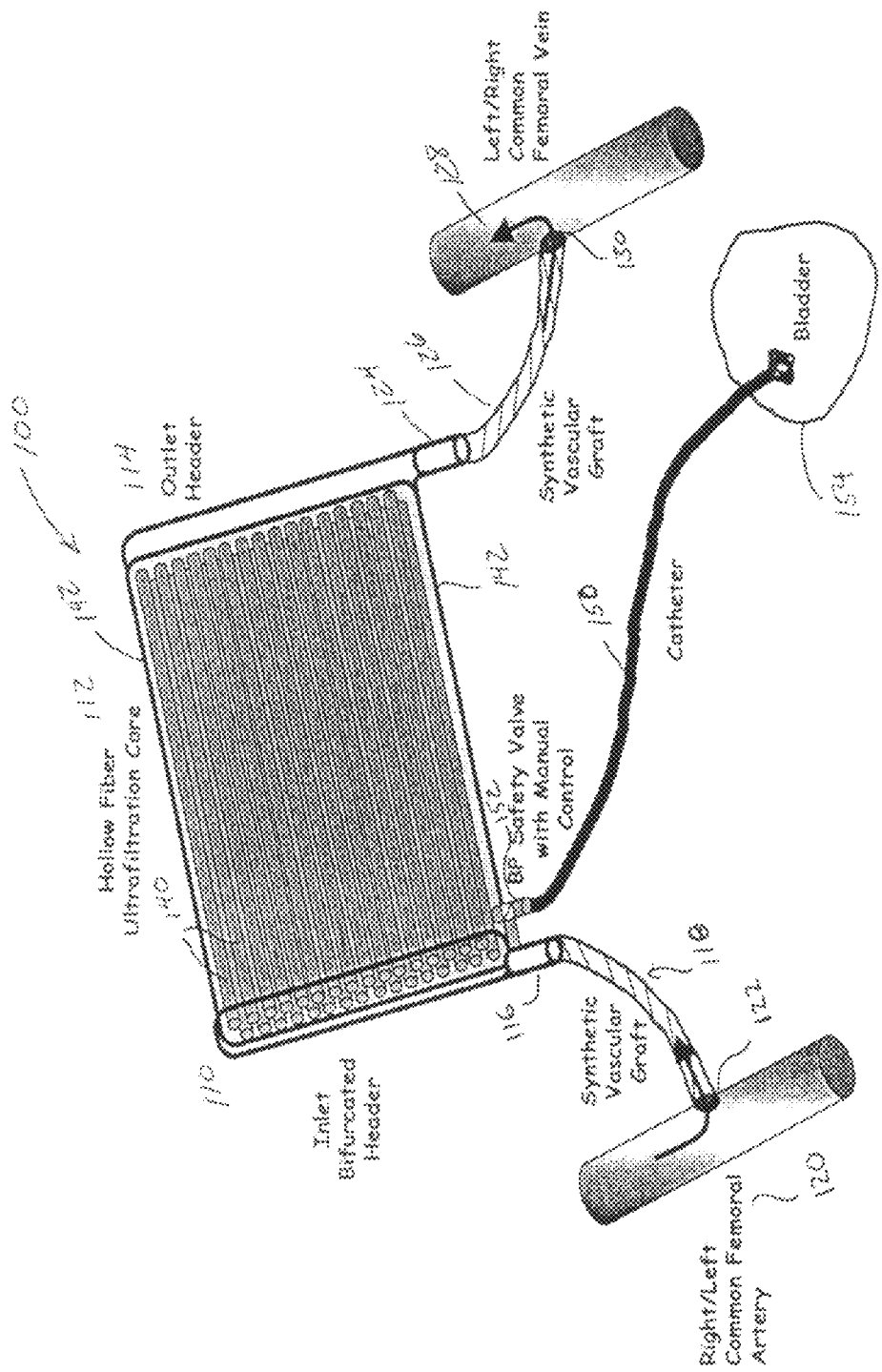
FIG. 8 is a schematic view an embodiment of an implantable fluid removing device.
Figure 9:
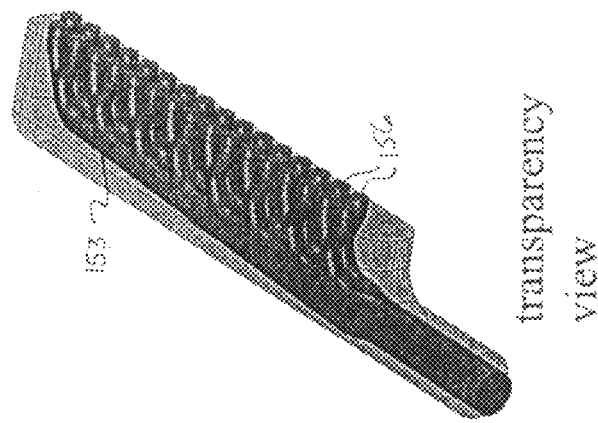
FIGS. 9-12 are a series of views of an embodiment of a header and flow paths through the header.

An embodiment of a fluid removing device that can be utilized in connection with an artificial kidney dialysis system as described herein is depicted in FIG. 8, which is also disclosed and described in WO2008/024434. FIG. 8 illustrates a schematic view of an embodiment of an ultrafiltration device 100 that is implantable into the body of a person. The embodiment includes an inlet header 110 and a hollow fiber ultrafiltration core 112 and an outlet header 114. The ultrafiltration core 112 is disposed between the inlet and outlet header in a fluid tight manner. The inlet header 110 includes an inlet conduit 116 that forms an attachment point for a graft material 118 from a femoral artery 120. In a preferred form, the vascular graft is a 6 mm PTFE graft. A cut is made into the femoral artery and the graft material 118 is attached to the femoral artery 120 at location 122 in a known manner. The headers 110 and 114 can alternately be referred to as manifolds or grooved headers.

Similarly the outlet header 114 includes an outlet conduit 124 so that a vascular graft 126 can be attached to the outlet header. In a preferred form, the vascular graft is a 6 mm PTFE graft. The other side of the graft 126 is attached to a femoral vein 128 at an attachment location 130.

Preferably the ultrafiltration device 100 is surgically implanted in a subcutaneous location near and above the groin, such as the retropubic space. This allows for shorter vascular grafts 118 and 126 to connect the ultrafiltration device 100 to the femoral artery 120 and femoral vein 130. In this location the valve 152 can be accessed and adjustments made without penetrating the skin, i.e. extracorporeally (the valve 152 is discussed further below). The surgical procedure can be performed using local anesthesia. The ultrafiltration device 100 can be removed or exchanged in a relatively simple surgical procedure.

The hollow fiber ultrafiltration core 112 includes a multiplicity of hollow fibers 140 that extend from the inlet header 110 and the outlet header 114 in a fluid tight manner. That is, blood that leaves the femoral artery 120 at the attachment point 122 and travels through the graft material 118 and into the header 110 will pass through the header into the plurality of hollow fibers 140. The housing protects the hollow fibers and also collects fluid that passes through the wall of the fibers.

The hollow fibers are connected to the outlet header 114 in a manner similar to the inlet header and fluid that passes through the fibers into the outlet header can be collected in the outlet header and pass through the graft material 126 and back into the bloodstream through the femoral vein.

The housing 142 includes a drain conduit 150 with a valve 152. The valve operates as a safety valve with a manual control so that the device can be properly regulated. The outlet of the drain conduit is configured to drain into the bladder 154. The drain conduit, in a preferred form, is a Filtrate Suprapubic Malecot Bladder Catheter available through Cook Medical, Bloomington, Ind. The Malecot catheter includes radially expandable distal end to secure the catheter within a bladder. Of course alternative catheters can be used to dispose of the fluid from the device. Additionally, the conduit can be directed outside the body and connected to an ostomy bag. Preferably the device 100 is substantially flat and the components of the device are substantially coplanar as shown in FIG. 8 in order to facilitate implantation of the device in the body of a patient.

The housing 142 and the ultrafiltration core 112 can be constructed out of flexible materials. This flexibility will permit the device 100 to bend or flex, further facilitating the implantation and maintenance of the device in the body of a patient. Alternatively, the housing 142 can be constructed from substantially inflexible material.

Figure 10:
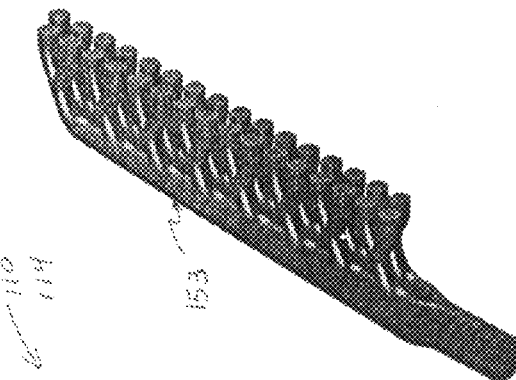
Figure 11:
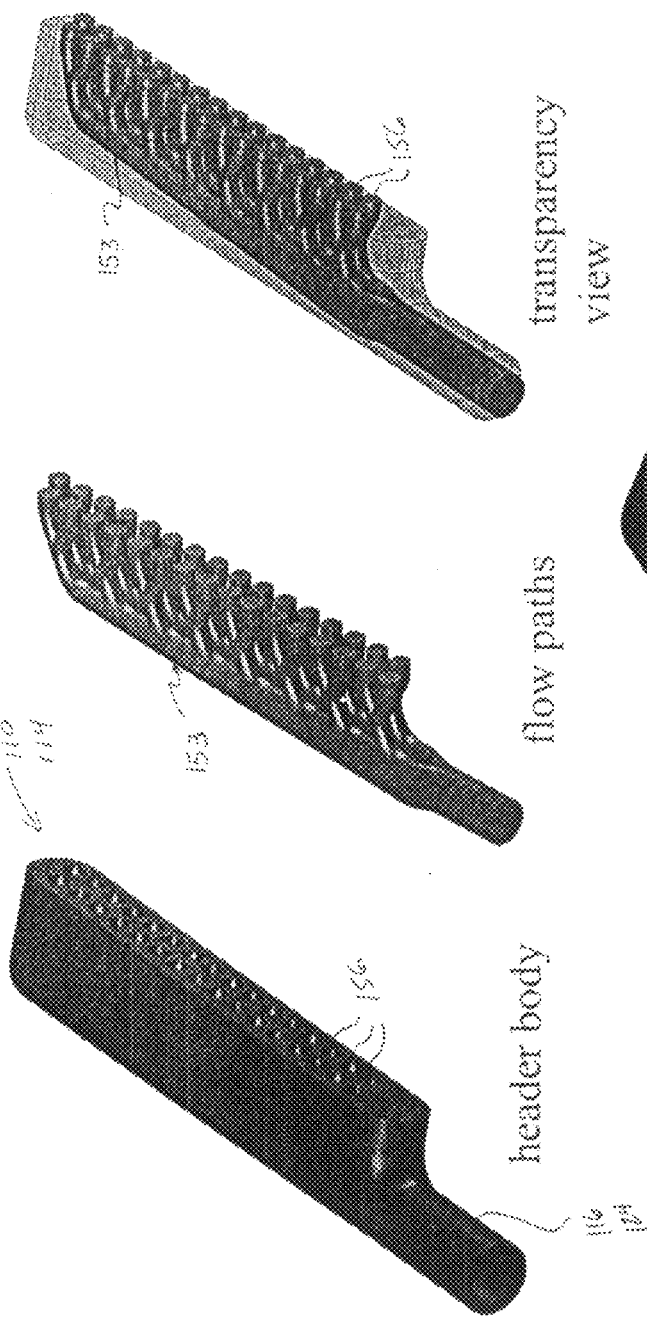
Figure 12:
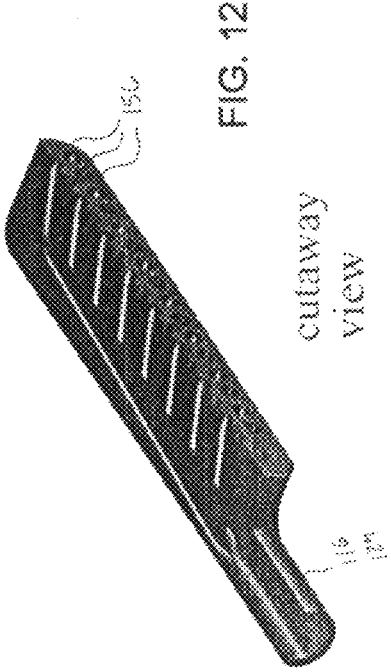

As shown in FIGS. 9-12, which are also disclosed and described in WO2008/024434, the inlet header 110 defines a flow path 153 beginning at the inlet conduit 116 which then is split or bifurcated into multiple separate flow passages 156. The separate flow passages 156 connect to the hollow fibers 140. Similarly, the outlet header 114 defines a flow path 153 beginning at the separate flow passages 156 at the juncture with the hollow fibers 140 and combines or converges the separate flow passages 156 into a single outlet conduit 124. The flow paths 153 defined by the inlet header 110 and outlet header 114 can be adapted to optimize the hydrodynamic forces acting on the fluid passing through the flow paths 153. FIG. 12 shows a partial cutaway view illustrating the flow path 153.

FIGS. 10 and 11 illustrate the flow paths 153 defined by the headers 110 and 114. As illustrated in FIG. 10-12, the header flow paths 153 are configured to have smoothly diverging/converging conduits. Reference numeral 153 in FIGS. 10 and 11 illustrates the volume of the flow paths 153 themselves. The headers 110 and 114 define the flow path 153. Flow passages 156 are adapted to fit the hollow tubes 140 of the ultrafiltration core 112. As in other embodiments, the connection preferably is made to be as smooth as possible (without discontinuities) so that the possibility of blood clotting is minimized.

The headers 110 and 114 including the corresponding flow paths 153 can be adapted to optimize the hydrodynamic forces acting on the blood as it passes through the flow paths 153 in a manner so as to minimize the disturbance of blood flow and to reduce or eliminate any stagnation points within the blood flow. In a preferred embodiment, there are thirty-two flow passages 156 in each of the headers 110 and 114.

In another preferred embodiment there are sixteen flow passages 156 in each of the headers 110 and 114. The angle and path of divergence for each flow passage 156 can be adapted to minimize thrombogenicity in blood flow, which eliminates or minimizes the amount of anticoagulant that is used to maintain the system clot-free throughout its intended use.

Figure 13:
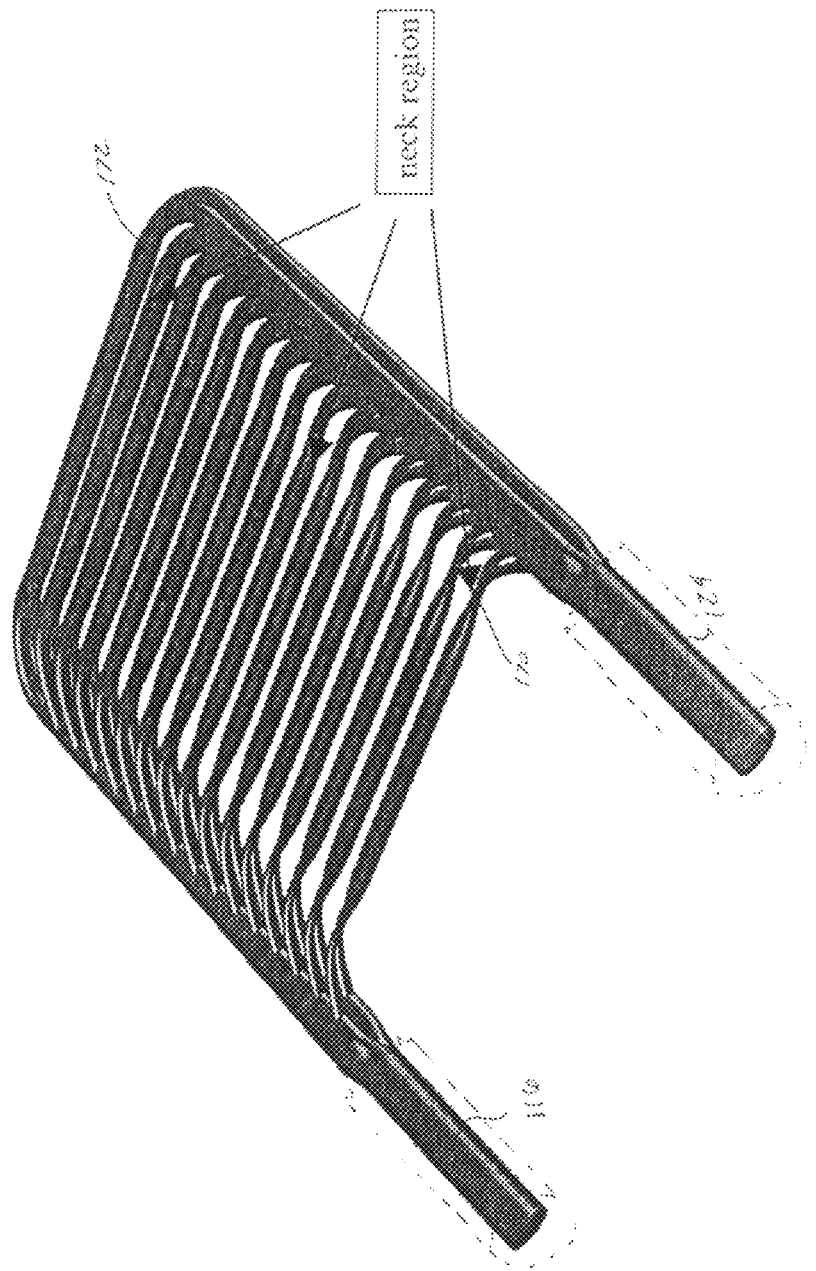

FIGS. 13 and 14, which are also disclosed and described in WO2008/024434, illustrate the flow path through one embodiment of the device. As shown in FIGS. 13 and 14 the flow path includes neck regions or necks, e.g. 170, 172. Neck regions are shown as constrictions or restrictions in the flow passages 156. Alternatively one or more of the neck regions may be located in the hollow fibers 140, preferably located towards the end of the hollow fibers 140. The neck regions closer to the header inlet conduit 116 and header outlet conduit 124, e.g. 170, are narrower (i.e., more flow restrictive) than the neck regions, e.g. 172, at the regions further away from the header inlet conduit 116 and header outlet conduit 124. The variation in neck region size can be adapted to provide for more uniform volume of blood flowing through each of the hollow fibers 140, minimize blood flow disturbance, and reduce or eliminate any stagnation points within the blood flow.

FIGS. 13 and 14 show an embodiment with neck regions, e.g. 170, 172, located in the inlet header 110 and the outlet header 114. Alternatively, neck regions could be present only in the inlet header 110 or the outlet header 114. Such an arrangement requires the neck regions to be more constricting as compared to the embodiment with neck regions located in both the inlet header 110 and the outlet header 114.

EXAMPLE

A GE Sepa™ lab scale crossflow membrane filtration unit was modified to enable the testing of membranes in a countercurrent diffusion mode. The unit was equipped with a Neosepta AFX-A0100 membrane. Peritoneal dialysis solution (1000 ml) spiked with 1.5 grams of urea was pumped across one side of the membrane. Deionized water (1000 ml) was circulated through the other side of the membrane and through a FMC-NA F6 dialysis cartridge (in which the hollow fibers were infused with a solution of washed urease). The deionized water was also pumped through 3 small cartridges containing ion exchange resins (two filled with Dowex 1 (OH) and one filled with a high capacity strong acid ion exchange resin from Rohm and Haas). It was found necessary to thoroughly wash the strong acid cation exchange resin, or material that leached from it deactivated the urease. Samples were removed periodically from both fluid loops and analyzed for calcium, magnesium, glucose, BUN, pH, and ammonia.

The analyses indicated that a significant portion of the urea diffused through the membrane and that there was minimal diffusion of the calcium, magnesium or sodium through the membrane. The urea that diffused through the membrane was hydrolyzed by the urease in the dialyzer hollow fibers to ammonia, which was in turn bound by the strong acid ion exchange resin. The combination of ion exchange resins maintained the pH of the solutions within a range in which the urease remained active over a period of 24 hours.

| PD Circuit | | | | | |
|---|---|---|---|---|---|
| Time (hr) | BUN (mg/dl) | Na (meq/L) | Mg (mg/dl) | Ca (mg/dl) | pH |
| 0.0 | 60.8 | 125 | 1.5 | 4.7 | 5.2 |
| 21.0 | 40.1 | 121 | 1.4 | 4.7 | 5.0 |
| 46.2 | 23.9 | 113 | 1.4 | 4.5 | 5.0 |

| RO Circuit | | | | | | |
|---|---|---|---|---|---|---|
| Time (hr) | BUN (mg/dl) | NH3 (μg/dl) | Na (meq/L) | Mg (mg/dl) | Ca (mg/dl) | pH |
| 0.0 | 0.0 | 0 | 0.0 | 0.0 | 0.0 | 6.4 |
| 21.0 | 0.0 | 0 | 0.0 | 0.1 | 0.0 | 6.3 |
| 46.2 | 5.1 | 30 | 0.0 | 0.0 | 0.0 | 6.0 |

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for the removal of uremic waste metabolites and excess fluid from a patient using a wearable peritoneal dialysis device and an implanted fluid removing device comprising:
   a) providing a volume of peritoneal dialysis solution;
   b) pumping the peritoneal dialysis solution into the peritoneal cavity of the patient through an access port, allowing the patient's uremic waste metabolites to diffuse through the peritoneal membrane and thereby come into contact with and dissolve in the peritoneal dialysis solution;
   c) pumping the peritoneal dialysis solution containing uremic waste metabolites out of the patient and into the device;
   d) filtering particulates and debris from the peritoneal dialysis solution containing uremic waste metabolites;
   e) regenerating the peritoneal dialysis solution containing uremic waste metabolites;
   f) returning the regenerated peritoneal dialysis solution to the patient's peritoneal cavity; and
   g) removing excess fluid from the blood stream of said patient with the implanted fluid removing device that comprises a plurality of hollow fiber membranes, said implanted fluid removing device connected to the blood stream of said patient by vascular grafts,
   thereby enabling the patient to maintain a relatively normal, active lifestyle.

2. The method of claim 1, wherein regenerating the peritoneal dialysis solution is performed using a replaceable cartridge having a urea removal layer that rejects calcium and magnesium ions.

3. The method of claim 1, further comprising controlling the pump flow rates and the timing and sequencing of the components of the device using a microprocessor.

4. A dialysis system for a patient comprising:
   a) a wearable peritoneal dialysis device comprising:
      i) a volume of peritoneal dialysis solution for infusion into and moving out of the patient's peritoneal cavity, allowing the patient's uremic waste metabolites to diffuse through the peritoneal membrane and thereby come into contact with and dissolve in the peritoneal dialysis solution, thereby removing from the patient uremic waste metabolites that have diffused into the peritoneal dialysis solution,
      ii) a closed fluid system loop for circulating the peritoneal dialysis solution from the patient, throughout the wearable peritoneal dialysis device and back into the patient,
      iii) at least one pump attached to the fluid system loop for infusing the peritoneal dialysis solution into the patient's peritoneal cavity and moving the peritoneal dialysis solution containing uremic waste metabolites out of the patient's peritoneal cavity and into the fluid system loop,
      iv) a filter attached to the fluid system loop for removing particulates and debris from the peritoneal dialysis solution containing uremic waste metabolites, and
      v) a urea removal device attached to the fluid system loop for regenerating the peritoneal dialysis solution; and
   b) an implanted fluid removing device that comprises a plurality of hollow fiber membranes, for removing excess fluid from the blood stream of said patient, said implanted fluid removing device connected to the blood stream of said patient by vascular grafts,
   thereby enabling the patient to maintain a relatively normal, active lifestyle.

5. The dialysis system of claim 4, wherein the urea removal device comprises a replaceable cartridge, said replaceable cartridge having a urea removal layer that rejects calcium and magnesium ions.

6. The dialysis system of claim 5, wherein the replaceable cartridge comprises:
   a) a purification layer for removing heavy metals, oxidants and other uremic waste metabolites from said peritoneal dialysis solution;
   b) a urea removal layer that rejects calcium and magnesium ions; and
   c) an ion-exchange layer for removing phosphate and sulfate from said peritoneal dialysis solution.

7. The dialysis system of claim 4, wherein the wearable peritoneal dialysis device further comprises a microprocessor in communication with the components of the fluid system loop, said microprocessor controlling the pump flow rates and the timing and sequencing of the components of the wearable peritoneal dialysis device.

8. The dialysis system of claim 4, wherein the wearable peritoneal dialysis device removes uremic waste metabolites from the patient.

9. The dialysis system of claim 4, further comprising sensors for monitoring the rate of fluid removal from a patient.

10. An integrated dialysis system for a patient comprising:
    a) a wearable peritoneal dialysis device; and
    b) an implanted fluid removing device comprising a plurality of hollow fiber membranes, for removing excess fluid from the blood stream of said patient, said implanted fluid removing device connected to the blood stream of said patient by vascular grafts,
    thereby enabling the patient to maintain a relatively normal, active lifestyle.

11. The dialysis system of claim 10, wherein the wearable peritoneal dialysis device is adapted for the removal of uremic waste metabolites from the patient.

12. The dialysis system of claim 10, further comprising sensors for monitoring the rate of fluid removal from a patient.

13. The dialysis system of claim 10, wherein the implanted fluid removing device comprises:
   a) a first header;
   b) a second header; and
   c) a filter comprising a plurality of hollow fiber membranes, the filter in fluid communication with the first header and the second header, the first header, the second header and the filter being adapted to define a flow path that provides substantially uniform flow of blood through each of the hollow fiber membranes.

14. The system of claim 13, further comprising:
   a) a first graft for connecting the vascular system of the patient to the first header;
   b) a second graft for connecting the second header to the vascular system of the patient;
   c) a housing adapted to collect fluid that passes through the filter; and
   d) a drain conduit connected to the housing.

15. The system of claim 13 wherein the first header and the second header are elongated members, and the first header, the second header and the filter are substantially coplanar.

16. The system of claim 13 wherein the filter is substantially permeable to water and substantially impermeable to blood cells and proteins.

17. The system of claim 13, wherein the first header has multiple outlets and the second header has multiple inlets, and the flow path includes one or more neck regions near each of one or more of the multiple outlets and one or more of the multiple inlets.

18. The system of claim 15, wherein the first header, the second header and the filter are each less than about 10 millimeters (mm) in thickness.

19. A method for the removal of uremic waste metabolites and excess fluid from a patient using a wearable peritoneal dialysis device and an implanted fluid removing device comprising:
   a) providing a volume of peritoneal dialysis solution;
   b) pumping the peritoneal dialysis solution into the peritoneal cavity of the patient through an access port, allowing the patient's uremic waste metabolites to diffuse through the peritoneal membrane and thereby come into contact with and dissolve in the peritoneal dialysis solution;
   c) pumping the peritoneal dialysis solution containing uremic waste metabolites out of the patient and into the device;
   d) filtering particulates and debris from the peritoneal dialysis solution containing uremic waste metabolites;
   e) regenerating the peritoneal dialysis solution containing uremic waste metabolites;
   f) returning the regenerated peritoneal dialysis solution to the patient's peritoneal cavity; and
   g) removing excess fluid from the blood stream of said patient with the implanted fluid removing device connected to the blood stream of said patient by vascular grafts, said fluid removing device comprising:
      i) a first header defining a first flow path having a single inlet and multiple outlets and a means for uniformly distributing fluid flow from the single inlet to the multiple outlets;
      ii) a second header defining a second flow path having multiple inlets and a single outlet;
      iii) a filter in fluid communication with said first header and said second header;
      iv) a first graft for connecting the vascular system of the patient to the single inlet;
      v) a second graft for connecting the single outlet to the vascular system of the patient;
      vi) a housing adapted to collect fluid that passes through the filter; and
      vii) a drain conduit connected to the housing.

20. The method of claim 19, wherein regenerating the peritoneal dialysis solution is performed using a replaceable cartridge having a urea removal layer that rejects calcium and magnesium ions.

21. A dialysis system for a patient comprising:
   a) a wearable peritoneal dialysis device comprising:
      i) a volume of peritoneal dialysis solution for infusion into and moving out of the patient's peritoneal cavity, allowing the patient's uremic waste metabolites to diffuse through the peritoneal membrane and thereby come into contact with and dissolve in the peritoneal dialysis solution, thereby removing from the patient uremic waste metabolites that have diffused into the peritoneal dialysis solution,
      ii) a closed fluid system loop for circulating the peritoneal dialysis solution from the patient, throughout the wearable peritoneal dialysis device and back into the patient,
      iii) at least one pump attached to the fluid system loop for infusing the peritoneal dialysis solution into the patient's peritoneal cavity and moving the peritoneal dialysis solution containing uremic waste metabolites out of the patient's peritoneal cavity and into the fluid system loop,
      iv) a filter attached to the fluid system loop for removing particulates and debris from the peritoneal dialysis solution containing uremic waste metabolites, and
      v) a urea removal device attached to the fluid system loop for regenerating the peritoneal dialysis solution; and
   b) an implanted fluid removing device for removing excess fluid from the blood stream of said patient, said implanted fluid removing device connected to the blood stream of said patient by vascular grafts, said fluid removing device comprising:
      i) a first header defining a first flow path having a single inlet and multiple outlets and a means for uniformly distributing fluid flow from the single inlet to the multiple outlets;
      ii) a second header defining a second flow path having multiple inlets and a single outlet;
      iii) a filter in fluid communication with said first header and said second header;
      iv) a first graft for connecting the vascular system of the patient to the single inlet;
      v) a second graft for connecting the single outlet to the vascular system of the patient;
      vi) a housing adapted to collect fluid that passes through the filter; and
      vii) a drain conduit connected to the housing.

22. The dialysis system of claim 21, wherein the urea removal device comprises a replaceable cartridge, said replaceable cartridge having a urea removal layer that rejects calcium and magnesium ions.

23. The dialysis system of claim 22, wherein the replaceable cartridge comprises:
   a) a purification layer for removing heavy metals, oxidants and other uremic waste metabolites from said peritoneal dialysis solution;
   b) a urea removal layer that rejects calcium and magnesium ions; and c) an ion-exchange layer for removing phosphate and sulfate from said peritoneal dialysis solution.

24. The method of claim 1, wherein the fluid removing device includes a drain conduit configured to drain into the bladder of the patient, thereby enabling the patient to maintain a relatively normal, active lifestyle.

25. The method of claim 4, wherein the fluid removing device includes a drain conduit configured to drain into the bladder of the patient, thereby enabling the patient to maintain a relatively normal, active lifestyle.

26. The dialysis system of claim 10, wherein the fluid removing device includes a drain conduit configured to drain into the bladder of the patient, thereby enabling the patient to maintain a relatively normal, active lifestyle.

27. A method for the removal of uremic waste metabolites and excess fluid from a patient using a wearable peritoneal dialysis device and an implanted fluid removing device comprising:
   a) providing a volume of peritoneal dialysis solution;
   b) pumping the peritoneal dialysis solution into the peritoneal cavity of the patient through an access port, allowing the patient's uremic waste metabolites to diffuse through the peritoneal membrane and thereby come into contact with and dissolve in the peritoneal dialysis solution;
   c) pumping the peritoneal dialysis solution containing uremic waste metabolites out of the patient and into the device;
   d) filtering particulates and debris from the peritoneal dialysis solution containing uremic waste metabolites;
   e) regenerating the peritoneal dialysis solution containing uremic waste metabolites;
   f) returning the regenerated peritoneal dialysis solution to the patient's peritoneal cavity; and
   g) removing excess fluid from the blood stream of said patient with the implanted fluid removing device that is connected to the blood stream of said patient by vascular grafts, and includes a drain conduit configured to drain into the bladder of the patient,
   thereby enabling the patient to maintain a relatively normal, active lifestyle.

28. The method of claim 27, wherein regenerating the peritoneal dialysis solution is performed using a replaceable cartridge having a urea removal layer that rejects calcium and magnesium ions.

29. A dialysis system for a patient comprising:
   a) a wearable peritoneal dialysis device comprising:
      i) a volume of peritoneal dialysis solution for infusion into and moving out of the patient's peritoneal cavity, allowing the patient's uremic waste metabolites to diffuse through the peritoneal membrane and thereby come into contact with and dissolve in the peritoneal dialysis solution, thereby removing from the patient uremic waste metabolites that have diffused into the peritoneal dialysis solution,
      ii) a closed fluid system loop for circulating the peritoneal dialysis solution from the patient, throughout the wearable peritoneal dialysis device and back into the patient,
      iii) at least one pump attached to the fluid system loop for infusing the peritoneal dialysis solution into the patient's peritoneal cavity and moving the peritoneal dialysis solution containing uremic waste metabolites out of the patient's peritoneal cavity and into the fluid system loop,
      iv) a filter attached to the fluid system loop for removing particulates and debris from the peritoneal dialysis solution containing uremic waste metabolites, and
      v) a urea removal device attached to the fluid system loop for regenerating the peritoneal dialysis solution; and
   b) an implanted fluid removing device for removing excess fluid from the blood stream of said patient, said implanted fluid removing device connected to the blood stream of said patient by vascular grafts and including a drain conduit configured to drain into the bladder of the patient,
   thereby enabling the patient to maintain a relatively normal, active lifestyle.

30. The dialysis system of claim 29, wherein the urea removal device comprises a replaceable cartridge, said replaceable cartridge having a urea removal layer that rejects calcium and magnesium ions.

31. An integrated dialysis system for a patient comprising:
   a) a wearable peritoneal dialysis device; and
   b) an implanted fluid removing device that includes a drain conduit configured to drain into the bladder of the patient, for removing excess fluid from the blood stream of said patient, said implanted fluid removing device connected to the blood stream of said patient by vascular grafts,
   thereby enabling the patient to maintain a relatively normal, active lifestyle.

32. The integrated dialysis system of claim 31, wherein the wearable peritoneal dialysis device is adapted for the removal of uremic waste metabolites from the patient.

* * * * *